(12) United States Patent
Stanescu et al.

(10) Patent No.: US 10,596,393 B2
(45) Date of Patent: Mar. 24, 2020

(54) RADIOTHERAPY SYSTEM INTEGRATING A RADIATION SOURCE WITH A MAGNETIC RESONANCE IMAGING APPARATUS WITH MOVABLE MAGNET COMPONENTS

(71) Applicant: UNIVERSITY HEALTH NETWORK, Toronto (CA)

(72) Inventors: Teodor Marius Stanescu, Toronto (CA); David Anthony Jaffray, Etobicoke (CA)

(73) Assignee: UNIVERSITY HEALTH NETWORK, Toronto, Ontario (CA)

(*) Notice: Subject to any disclaimer, the term of this patent is extended or adjusted under 35 U.S.C. 154(b) by 693 days.

(21) Appl. No.: 14/417,631

(22) PCT Filed: Jul. 29, 2013

(86) PCT No.: PCT/CA2013/000673
§ 371 (c)(1),
(2) Date: Jan. 27, 2015

(87) PCT Pub. No.: WO2014/015421
PCT Pub. Date: Jan. 30, 2014

(65) Prior Publication Data
US 2015/0217136 A1    Aug. 6, 2015

Related U.S. Application Data

(60) Provisional application No. 61/676,576, filed on Jul. 27, 2012.

(51) Int. Cl.
*A61N 5/10*    (2006.01)
*A61B 5/055*   (2006.01)
(Continued)

(52) U.S. Cl.
CPC ............ *A61N 5/1049* (2013.01); *A61B 5/055* (2013.01); *A61B 6/4417* (2013.01);
(Continued)

(58) Field of Classification Search
None
See application file for complete search history.

(56) References Cited

U.S. PATENT DOCUMENTS 5,023,554 A      6/1991   Cho et al.
5,153,546 A *   10/1992   Laskaris ............ G01R 33/3806
                                                              324/318
(Continued)

FOREIGN PATENT DOCUMENTS

CA        2880312 A1    1/2014
EP        0517452 B1    8/1998
(Continued)

OTHER PUBLICATIONS

Arpinar et al., "Magnetic Resonance Imaging in Inhomogeneous Magnetic Fields with Noisy Signal", 2008, ECIFMBE Proceedings, 22, pp. 410-413.*

(Continued)

*Primary Examiner* — Katherine L Fernandez
*Assistant Examiner* — Yi-Shan Yang
(74) *Attorney, Agent, or Firm* — Bereskin & Parr LLP/S.E.N.C.R.L., s.r.l.; Tony Orsi

(57) ABSTRACT

A Radio-Therapy (RT) system includes an integrated radiation source and a Magnetic Resonance Imaging (MRI) system that implements a method for providing a variable imaging Field Of View (FOV). The FOV can be tailored for various RT-specific applications such as, but not limited to, patient setup verification and real-time tumor tracking, for example, as well as for various imaging volumes of interest.

22 Claims, 17 Drawing Sheets

(51) Int. Cl.
  *A61B 6/00* (2006.01)
  *G01R 33/48* (2006.01)
  *G01R 33/567* (2006.01)
  *A61B 5/00* (2006.01)

(52) U.S. Cl.
  CPC ....... *G01R 33/4808* (2013.01); *G01R 33/567* (2013.01); *A61B 5/0035* (2013.01); *A61N 2005/1055* (2013.01); *A61N 2005/1091* (2013.01)

(56) References Cited

U.S. PATENT DOCUMENTS

| | | | |
|---|---|---|---|
| 5,304,930 | A | 4/1994 | Crowley et al. |
| 5,935,065 | A | 8/1999 | Rose, Jr. et al. |
| 6,374,132 | B1 | 4/2002 | Acker et al. |
| 6,708,054 | B2 | 3/2004 | Shukla et al. |
| 7,309,986 | B2 | 12/2007 | Epstein et al. |
| 7,375,357 | B2* | 5/2008 | Kaufman ........... A61N 5/10 250/396 ML |
| 7,907,987 | B2 | 3/2011 | Dempsey |
| 8,915,833 | B1* | 12/2014 | Sahadevan ........ A61N 5/1027 600/1 |
| 2001/0001807 | A1 | 5/2001 | Green |
| 2007/0139148 | A1* | 6/2007 | McDougall ........ G01R 33/381 335/213 |
| 2008/0208036 | A1 | 8/2008 | Amies et al. |
| 2009/0149735 | A1* | 6/2009 | Fallone ............. A61N 5/1049 600/411 |
| 2009/0208074 | A1* | 8/2009 | Wiersma ............... G06T 7/251 382/128 |
| 2009/0310841 | A1* | 12/2009 | Biglieri ............. A61B 5/055 382/131 |
| 2010/0174172 | A1 | 7/2010 | Ein-Gal |
| 2010/0239066 | A1* | 9/2010 | Fahrig ............... A61N 5/1049 378/65 |
| 2010/0049030 | A1 | 10/2010 | Saunders et al. |
| 2011/0118588 | A1 | 5/2011 | Komblau et al. |
| 2011/0175694 | A1 | 7/2011 | Fallone et al. |
| 2011/0196227 | A1 | 8/2011 | Gross et al. |
| 2011/0201919 | A1 | 8/2011 | Allen et al. |
| 2011/0218420 | A1 | 9/2011 | Carlone et al. |
| 2011/0241684 | A1 | 10/2011 | Dempsey et al. |
| 2011/0260729 | A1 | 10/2011 | Carlone et al. |
| 2012/0025824 | A1* | 2/2012 | Harder ............... G01R 33/543 324/309 |

FOREIGN PATENT DOCUMENTS

| | | |
|---|---|---|
| EP | 2535086 A1 | 12/2012 |
| EP | 2877089 A1 | 6/2015 |
| WO | 9852465 A1 | 11/1998 |
| WO | 2007061438 A2 | 5/2007 |
| WO | 2012063158 A1 | 5/2012 |
| WO | 2014015421 A1 | 1/2014 |

OTHER PUBLICATIONS

Xu et al., "Homogeneous Magnet Design Using Linear Programming," Mar. 2000, IEEE Transactions on Magnetics, vol. 36, No. 2, pp. 476-483.*
World Health Organization, http://www.who.int (2012).
B. Fallone, B. Murray, S. Rathee, T. Stanescu, S.Steciw, S. Vidakovic, E. Blosser and D. Tymofichuk, :First MR images obtained during megavoltage photob irradation from a prototype integrated linac-MR system, Med. Phys. 36 (6) Jun. 2009, 2084-2088.
B.W. Raaymakers, J.J. Lagendijk, J. Overweg, J. G. Kok, A. J. Raaijmakers, E. M. Kerkhof, R. W. van der Put, I. Meijing, S. P. Crijns, F. Benedosso, M. van Vulpen, C. H. de Graaff, J. Allen and K. J. Brown, "Integrating a 1.5 T MRI scanner with a 6 MV accelerator: proof of concept," Physics in medicine and biology, May 19, 2009, N229-N237.
ViewRay, http://www.viewray.com/system, "A complete MRI-guided radiation therapy system".
J. Dempsey, B. Dionne, J. Fitzsimmons and e. al., "WE-E-ValA-06: A Real-time MRI Guided External Beam Radiotherapy Delivery System," Medical Physics, Jul. 11, 2006, 2254.
D. Jaffray, M. Carlone, C. Menard and S. Breen, "Image-guided Radiation Therapy: Emergence of MR-Guided Radiation Treatment (MRgRT) Systems," Proc. SPIE vol. 7622, 762202 (2010).
T. Tadic, D. Jaffray and T. Stanescu, "MRIgRT facility design: magnetic field decoupling of an MRI-on-rails from a linear accelerator," 5th NCIGT and NIH Image Guided Therapy Workshop, Boston, USA (2012).
S. P. Crijns, J. G. Kok, J. J. Lagendijk and B. W. Raaymakers, "Towards MRI-guided linear accelerator control: gating on an MRI accelerator," Physics in medicine and biology 56 (15), 4815-4825, Jul. 13, 2011.
J. Yun, M. Mackenzie, S. Rathee, D. Robinson and B. G. Fallone, "An artificial neural network (ANN)-based lung-tumor motion predictor for intrafractional MR tumor tracking," Medical physics 39 (7), 4423-4433, Jun. 28, 2012.
J. St Aubin, S. Steciw and B. G. Fallone, "Magnetic decoupling of the linac in a low field biplanar linac-MR system," Medical physics 37 (9), 4755-4761, Aug. 17, 2010.
J. St Aubin, D. M. Santos, S. Steciw and B. G. Fallone, "Effect of longitudinal magnetic fields on a simulated in-line 6 MV linac," Medical physics 37 (9), 4916-4923, Aug. 24, 2010.
B. Burke, M. Lamey, S. Rathee, B. Murray and B. G. Fallone, "Radio frequency noise from clinical linear accelerators," Physics in medicine and biology 54 (8), 2483-2492, Apr. 1, 2009.
M. Lamey, B. Burke, E. Blosser, S. Rathee, N. De Zanche and B. G. Fallone, "Radio frequency shielding for a linac-MRI system," Physics in medicine and biology 55 (4), 995-1006, Jan. 20, 2010.
C. Kirkby, T. Stanescu, S. Rathee, M. Carlone, B. Murray and B. G. Fallone, "Patient docimetry for hybrid MRI-radiotherapy systems," Medical physics 35 (3), 1019-1027, Feb. 21, 2008.
C. Kirkby, B. Murray, S. Rathee and B. G. Fallone, "Lung dosimetry in a linac-MRI radiotherapy with a longitudinal magnetic field", Medical physics 37 (9), 4722-4732 (2010).
A. J. Raaijmakers, B.W. Raaymakers, J.J. Lagendijk, "Integrating a MRI scanner with 6 MV radiotherapy accelerator: dose increase at tissue-air interfaces in a lateral magnetic field due to returning electrons", Physics in medicine and biology 50 (7), 1363-1376 (2005).
A. J. Raaijmakers, B.W. Raaymakers, J.J. Lagendijk, "Experimental verification of magnetic field dose effects for the MRI-accelerator," Physics in medicine and biology 52 (14), 4283-4291 (2007).
B. M. Oborn, P. E. Metcalfe, M. J. Butson, A. B. Rosenfeld and P. J. Keall, "Electron contamination modeling and skin dose in 6MV longitudinal field MRIgRT: impact of the MRI and MRI fringe field", Medical physics 39 (2), 874 (2012).
A. Keyvanloo, B. Burke, B. Warkentin, T. Tadic, S. Rathee, C. Kirkby, D. M. Santos and B. G. Fallone, "Skin dose in longitudinal and transverse lanic-MRIs using Monte Carlo and realistic 3D MRI field models", Medical physics 39 (10), 6509-6521 (2012).
B. Burke, B. G. Fallone, S. Rathee, "Radiation induced currents in MRI RF coils: application to linac/MRI integration", Physics in medicine and biology 55 (3), 735-746 (2010).
B. Burke, A. Ghila, B. G. Fallone, S. Rathee, "Radiation induced current in the RF coils of integrated linac-MR systems: The effect of buildup and magnetic field", Medical physics 39 (8), 5004-5014 (2012).
S. J. Hoogcarspel, S. P. Crijns, J. J. Lagendijk, M. van Vulpen and B. W. Raaymakers, "The feasibility of using a conventional flexible RF coil for an online MR-guided radiotherapy treatment", Physics in medicine and biology 58 (6), 1925-1932 (2013).
J. St Aubin, S. Steciw and B. G. Fallone, "Effect of transverse magnetic fields on a simulated in-line 6 MV linac", Physics in medicine and biology 55 (16), 4861-4869 (2010).
D. E. Constantin, R. Fahrig and P. J. Keall, "A study of the in-line and perpendicular magnetic fields on beam characteristics of electron guns in medical linear accelerators", Medical physics 38 (7), 4174-4185 (2011).

(56) References Cited

OTHER PUBLICATIONS

D. M. Santos, J. St Aubin, B. G. Fallone and S. Steciw, Magnetic shielding investigation for a 6 MV in-line linac within the parallel configuration of a linac-MR system, Medical physics 39 (2), 788-797 (2012).
A. J. Raaijmakers, B. W. Raaymakers and J. J. Lagendijk, "Magnetic-field-induced dose effects in MR-guided radiotherapy systems: dependence on the magnetic field strength", Physics in medicine and biology 53 (4), 909-923 (2008).
B. W. Raaymakers, A. J. Raaijmakers, A. N. Kotte, D. Jette and J. J. Lagendijk, "Integrating a MRI scanner with a 6 MV radiotherapy accelerator: dose deposition in a transverse magnetic field", Physics in medicine and biology 49 (17), 4109-4118 (2004).
H. Xu, "Homogenous Magnet Design Using Linear Programming", IEEE Transactions on Magnetics 36 (2), 476-483 (2000).
S. Russenschuck, "Synthesis, Inverse Problems and Optimization in Computational Electromagnetics", Int J Numerical Modelling : Electronic Networks, Devices and Fields 9, 45-57 (1996).
S. Crozier and D. Doddrell, "Compact MRI Magnet Design by Stochastic Optimization", J Magn Reson 127 (2), 233-237 (1997).
S. Crozier, L. Forbes and D. Doddrell, "A novel, open access, elliptical cross-section magnet for paediatric MRI", Meas Sci Technol 9 (1998), 113-119.
W. Smythe, "Magnetic Interaction of Current", Static and Dynamic Electricity (McGraw-Hill, 1950).
D. Thayer, "Imaging techniques and hardware for inhomogeneous MRI", Master of Science thesis. Brigham Young University, 2004.
V. Arpinar and B. Eyuboglu, "Magnetic Resonance Imaging in Inhomogeneous Magnetic Field with Noisy Signal", IFMBE Proceedings 22, 410-413 (2008).
V. Arpinar and B. Eyuboglu, "Magnetic Resonance Signal Analysis in Inhomogeneous Magnetic Field", IFMBE Proceedings 25, 432-435 (2009).
A. Yilmaz and B. Eyuboglu, RF Coil for MRI Applications in Inhomogeneous Main Magnetic Field, IFMBE Proceedings 14 (3), 1480-1483 (2003).
B. Raaymakers, J. de Boer, C. Knox, S. Crijns, K. Smit, M. Stam, M. Bosch, J. Kok and J. Lagendijk, "Integrated megavoltage portal imaging with a 1.5 T MRI linac", Physics in medicine and biology 56 (19), N207-214 (2011).
C. M. Lai, "Reconstrctng NMR images from projections under inhomogeous magnetic field and non-linear field gradients", Physics in medicine and biology 28 (8), 925-938 (1983).
C. Lai, "Reconstructing NMR images under fields with large inhomogeneties", J. Phys E: Sci Instrum 15, 1093-1100 (1982).
C. Epstein, "Magnetic resonance imaging in inhomogeous fields", Inverse Problems 20, 753-780 (2004).
C. Epstein and J. Magland, "Slant-slice imaging with an inhomogeous field", Proc Intl Soc Mag Reson Med 14, 3556 (2006).
C. L. Epstein and J. Magland, "A Novel Technique for Imaging with Inhomogeous Fields", J Magn Reson 183 (2), 183-192 (2006).
International Preliminary report on Patentability (IPRP), international application No. PCT/CA2013/000673, dated Feb. 5, 2015.
K. Wachowicz, T. Tadic and B. G. Fallone, "Geometric distortion and shimming considerations in a rotating MR-linac design due to the influence of low-level external magnetic fields", Med. Phys. 39 (5), 2659-2668 (May 2012).
Supplementary European Search Report, EP application No. EP 13823480, dated Mar. 16, 2016.
Tadic et al., "Design and Optimization of a Novel Bored Biplanar Permanent-Magnet Assembly for Hybrid Magnetic Resonance Imaging Systems", IEEE Transactions on Magnetics, 2010, 46(12): 4052-4058.
Tadic et al., "Design and Optimization of Superconducting MRI Magnet Systems With Magnetic Materials", IEEE Transactions on Applied Superconductivity, 2012, 22(2): 4400107 (7 pages).

* cited by examiner

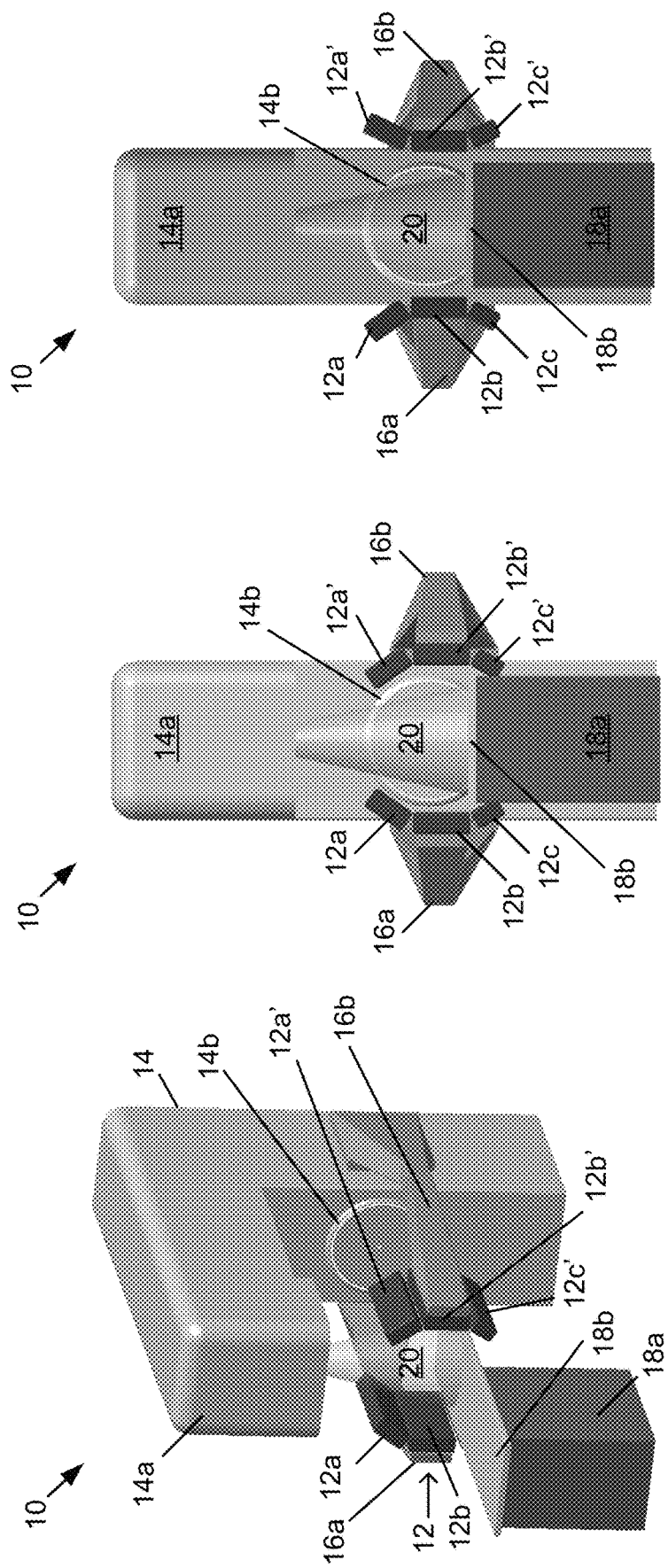

RADIOTHERAPY SYSTEM INTEGRATING A RADIATION SOURCE WITH A MAGNETIC RESONANCE IMAGING APPARATUS WITH MOVABLE MAGNET COMPONENTS

FIELD

The various embodiments described herein generally relate to Radiotherapy systems and associated methods for generating Magnetic Resonance (MR) images with greater flexibility.

BACKGROUND

Each year 12.7 million people worldwide are diagnosed with cancer and there are 7.6 million deaths from the disease.[1] Radio-Therapy (RT) plays a pivotal role in the management of various types of cancer, since approximately 50% of all cancer cases being treated with this type of therapy. RT consists of the planning and accurate delivery of lethal doses of X-ray radiation to tumor tissues (i.e. within 1-2 mm) while sparing the surrounding healthy tissues. One of the key components in achieving these objectives is high quality imaging, as it is vital to visualize and localize the anatomy embedding the disease site. Without pinpointing the extent of cancerous tissues, the chances of hitting and killing the treatment targets are limited, leading to poor patient outcomes.

In recent years, advanced Image Guided Radio-Therapy (IGRT) techniques, aimed to guide the daily patient's treatment setup, have been proposed for clinical use. These IGRT techniques comprise: a) Cone-Beam Computed Tomography (CBCT) combined with a linear accelerator (linac), b) ultrasound imaging, c) tomotherapy, d) portal image verification relying on transmission images of bony anatomy or implanted fiducial markers, generated by the linac's Mega-Voltage (MV) beam, and e) Kilo-Voltage (kV) images produced by an X-ray tube mounted on the linac gantry. All of these imaging modalities are used separately except for kV and MV imaging which may be used together. The main benefits of using such imaging modalities include the reduction of safety margins leading to higher local tumor control and reduced normal tissue toxicity via safe dose escalation.

RT relies heavily on X-ray-based imaging for treatment guidance. X-ray transmission-based images (kV or MV) show great bony detail but are inherently limited in resolving soft-tissue organ structures. The ideal imaging technique for RT would feature the ability to: a) clearly distinguish soft-tissue structures (i.e. tumor target and organs) from the surrounding anatomical background, and b) capture and dynamically track tumor target and internal organ motion manifested as the change in shape and location of the organ volume (e.g., due to breathing). A prime candidate with the potential of fulfilling these demanding requirements is Magnetic Resonance Imaging (MRI). Due to its excellent soft-tissue contrast, MRI has proven to be the preferred imaging modality for the delineation of anatomical structures in RT. Other significant benefits of MRI include its capability for multiplanar and fast imaging as well as its non-invasive technique for generating images (i.e. no harmful radiation is delivered to patient).

SUMMARY OF VARIOUS EMBODIMENTS

In a broad aspect, at least one embodiment described herein provides an MRI system for generating MR images of a volume of interest from an object. The MRI system comprises an operator unit for controlling the operation of the MRI system; and an MRI scanner coupled to the operator unit and configured to perform MRI imaging of the volume of interest, the MRI scanner including: interface circuitry for coupling to the operator unit; at least one moveably adjustable magnetic component that can be moved to different positions relative to the volume of interest for performing different MR imaging of the volume of interest; and a magnet positioning assembly that is coupled to the at least one moveably adjustable magnetic component to move the at least one moveably adjustable magnetic component to one of the different positions.

In at least some embodiments, the magnet positioning assembly may be configured to move the at least one movably adjustable magnet component toward or away from the object to a first position for imaging a Region 1 that is sufficient to perform single-slice imaging or multiple-slice imaging with a reduced Field of View (FOV).

In at least some embodiments, the Region 1 has a reduced slab volume with a homogeneous magnetic field produced by the MRI scanner at a central axis.

In at least some embodiments, the magnet positioning assembly may be configured to move the at least one movably adjustable magnet component to a second position for imaging a Region 2 for increasing imaging volume.

In at least some embodiments, the MRI scanner may comprise a pair of upper magnet components, a pair of central magnet components and a pair of lower magnet components with all of the pairs being disposed on either side of the object, wherein at least one of the pairs of magnet components are movably adjustable.

In at least some embodiments, the pairs of upper and lower magnet components may be movably adjustable.

In at least some embodiments, the pair of central magnet components may be movably adjustable.

In at least some embodiments, each pair of magnet components may be movably adjustable.

In at least some embodiments, the FOV of the MRI scanner may be extended for imaging the Region 2 by adjusting the position of the pairs of upper and lower magnet components.

In at least some embodiments, the FOV of the MRI scanner may be reduced for imaging the Region 1 by adjusting the position of the pair of central magnet components.

In at least some embodiments, the magnet positioning assembly may comprise at least one moveable robotic arm for moving the at least one adjustably moveable magnet component.

In another aspect, at least one embodiment described herein provides a Radio-Therapy (RT) system for at least one of radiation treatment, patient setup verification, real-time tracking of organ motion during radiation treatment delivery and MR imaging. The system comprises a radiation source configured to generate a treatment beam for an object during use; and an MRI scanner coupled to the radiation source, the MRI scanner being defined according to any one of the preceding paragraphs with at least one movably adjustable magnet component that is moveable between various positions to image at least one region of the object before, during or after treatment with the treatment beam.

In at least some embodiments, the RT system comprises a first mode of operation in which certain movably adjustable magnet components of the MRI scanner are moved away from the object to facilitate real-time imaging during treatment delivery and a second mode of operation in which certain movably adjustable magnet components of the MRI scanner are moved closer to the object to generate larger imaging volumes.

In at least some embodiments, the RT system further comprises a processor configured to perform single slice reconstruction on MRI imaging data obtained for the object and assumes a uniform magnetic field is generated by the MRI scanner.

In at least some embodiments, the processor is further configured to perform image reconstruction based on assuming a non-uniform magnetic field is generated by the MRI scanner and based on prior knowledge of a spatial distribution of inhomogeneities of the magnetic field for the second region.

In at least some embodiments, the radiation source is a linac and the MRI scanner is coupled to a housing of the linac.

In at least some embodiments, the radiation source is a linac and the MRI scanner and the linac are mechanically coupled to a common gantry.

In at least some embodiments, the MRI scanner is configured to generate a magnetic field for imaging a single slice or a single slice and a second region.

In at least some embodiments, the movably adjustable magnet components are mounted such that the magnetic field in the imaging volume is oriented in-line to the treatment beam thereby preserving the capability for kV imaging, and the RT system further comprises kV imaging components that are mounted and oriented at 90° with respect to the direction of the treatment beam thereby allowing for dual MRI and X-ray kV imaging.

In at least some embodiments, the RT system is configured to perform dual imaging including MRI and X-ray kV imaging during rotation of the linac and magnet components of the MRI scanner around the object.

In at least some embodiments, the RT system further comprises an x-ray megavoltage (MV) panel detector that is mounted to face the treatment beam thereby allowing for dual MRI and X-ray MV imaging.

In at least some embodiments, the object comprises an individual, a test subject, a patient, an animal specimen or a phantom.

In another aspect, at least one embodiment described herein provides a method for performing MR imaging for a desired imaging volume of an object using an MRI scanner having at least one moveably adjustable magnet component. The method comprises determining the desired imaging volume for the object; positioning the object for imaging by the MRI scanner; moving the at least one moveable magnet of the MRI scanner closer to or farther away from the desired imaging volume to position an actual imaging volume at the desired imaging volume; and performing MR imaging of the object.

In at least some embodiments, the at least one movably adjustable magnet component is moved toward or away from the object to a first position for imaging a Region 1 that is sufficient to perform single-slice imaging or multiple-slice imaging with a reduced Field of View (FOV).

In at least some embodiments, the Region 1 has a reduced slab volume with a homogeneous magnetic field produced by the MRI scanner at a central axis.

In at least some embodiments, the at least one movably adjustable magnet component is moved to a second position for imaging a Region 2 for increasing imaging volume.

In at least some embodiments, the MRI scanner comprises a pair of upper magnet components, a pair of central magnet components and a pair of lower magnet components with all of the pairs being disposed on either side of the object, wherein the method comprises moving the position of at least one of the pairs of magnet components closer to or farther away from the desired imaging volume.

In at least some embodiments, the method comprises moving the pairs of upper and lower magnet components closer to or farther away from the volume of interest for MR imaging.

In at least some embodiments, the method comprises moving the central magnet components closer to or farther away from the volume of interest for MR imaging.

In at least some embodiments, the method comprises moving each pair of magnet components closer to or farther away from the volume of interest for MR imaging.

In at least some embodiments, the method comprises extending the FOV of the MRI scanner for imaging the Region 2 by adjusting the position of the pairs of upper and lower magnet components.

In at least some embodiments, the method comprises reducing the FOV of the MRI scanner for imaging the Region 1 by adjusting the position of the pair of central magnet components.

In at least some embodiments, the method comprises using at least one moveable robotic arm for moving the at least one adjustably moveable magnet component.

In another aspect, at least one embodiment described herein provides a method for performing at least one of radiation treatment, patient setup verification, real-time tracking of organ motion during radiation treatment delivery and MR imaging by using an MRI scanner and a radiation source, the MRI scanner having at least one movably adjustable magnet with an adjustable radial distance relative to a desired imaging volume for the object. The method comprising performing patient setup for a treatment location with respect to the radiation source; adjusting the position of the at least one movably adjustable magnet of the MRI scanner to be closer to or farther away from the desired imaging volume; obtaining MR images and adjusting the patient setup based on the MR images; applying radiation treatment to the object with simultaneous real-time MR imaging; and performing further MR imaging for post-treatment assessment of the object.

In at least some embodiments, the method comprises operating in a first mode of operation in which certain movably adjustable magnet components of the MRI scanner are moved away from the object to facilitate real-time imaging during treatment delivery and a second mode of operation in which certain movably adjustable magnet components of the MRI scanner are moved closer to the object to generate larger imaging volumes.

In at least some embodiments, the method further comprises using a processor to perform single slice reconstruction on MRI imaging data obtained for the object and assuming a uniform magnetic field is generated by the MRI scanner.

In at least some embodiments, the method further comprises using the processor to perform image reconstruction based on assuming a non-uniform magnetic field is generated by the MRI scanner and based on prior knowledge of a spatial distribution of inhomogeneities of the magnetic field for the second region.

In at least some embodiments, the method further comprises configuring the MRI scanner to generate a magnetic field for imaging a single slice or a single slice and a second region.

In at least some embodiments, the movably adjustable magnet components are mounted such that the magnetic field in the imaging volume is oriented in-line to the treatment beam thereby preserving the capability for kV imaging, and kV imaging components are mounted and oriented at 90° with respect to the direction of the treatment beam and the method further comprises performing dual MRI and X-ray kV imaging.

In at least some embodiments, the method further comprises performing dual imaging including MRI and X-ray kV imaging during rotation of the radiation source and magnet components of the MRI scanner around the object.

In at least some embodiments, an x-ray megavoltage (MV) panel detector is mounted to face the treatment beam and the method further comprises performing dual MRI and X-ray MV imaging.

In another aspect, at least one embodiment described herein provides a computer readable medium comprising a plurality of instructions that are executable on a processor of a system for adapting the system to implement a method for performing MR imaging for a desired imaging volume of an object using an MRI scanner having at least one moveably adjustable magnet component, wherein the method is as defined above.

In another aspect, at least one embodiment described herein provides a computer readable medium comprising a plurality of instructions that are executable on a processor of a system for adapting the system to implement a method for performing MR imaging in combination with radiation treatment by using an MRI scanner and a radiation source, the MRI scanner having at least one movably adjustable magnet with an adjustable radial distance relative to a desired imaging volume for the object, wherein the method is as defined above.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment and the figures will now be briefly described.

FIGS. 7A-7C are conceptual drawings of various views of an example embodiment of an MR-linac system in accordance with the teachings herein;

Figure 1A:
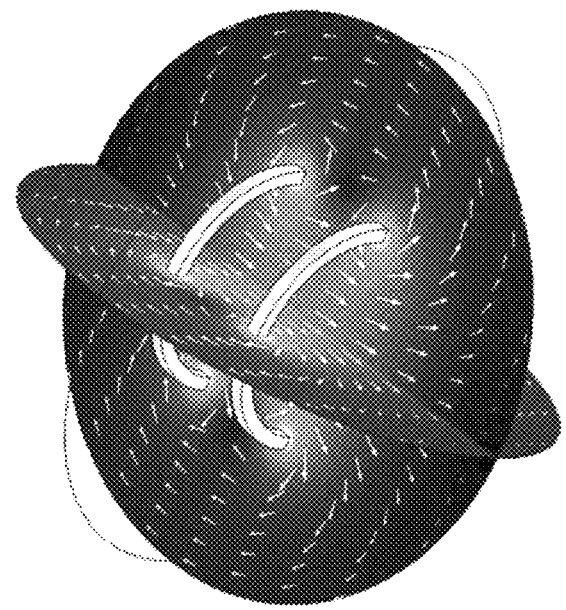
FIGS. 1A-1C are perspective, (x,y)-plane and (y,z)-plane views, respectively, depicting the spatial distribution of a Magnetic field ($B_0$) generated by an arbitrary coil pair.

Further aspects and advantages of the embodiments described herein will appear from the following description taken together with the accompanying drawings.

DETAILED DESCRIPTION OF THE EMBODIMENTS

Various apparatuses or processes will be described below to provide an example of at least one embodiment of the claimed subject matter. No embodiment described below limits any claimed subject matter and any claimed subject matter may cover processes, apparatuses, devices or systems that differ from those described below. The claimed subject matter is not limited to apparatuses, devices, systems or processes having all of the features of any one apparatus, device, system or process described below or to features common to multiple or all of the apparatuses, devices, systems or processes described below. It is possible that an apparatus, device, system or process described below is not an embodiment of any claimed subject matter. Any subject matter that is disclosed in an apparatus, device, system or process described below that is not claimed in this document may be the subject matter of another protective instrument, for example, a continuing patent application, and the applicants, inventors or owners do not intend to abandon, disclaim or dedicate to the public any such subject matter by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It should also be noted that the terms "coupled" or "coupling" as used herein can have several different meanings depending in the context in which the term is used. For example, the term coupling can have a mechanical or electrical connotation. For example, as used herein, the terms the terms "coupled" or "coupling" can indicates that two elements or devices can be directly connected to one another or connected to one another through one or more intermediate elements or devices via an electrical element, electrical signal or a mechanical element such as but not limited to, a wire or cable, for example, depending on the particular context.

Furthermore, the term "linac" used in the context of this application means any radiation source such as, but not limited to, x-ray, Co-60, protons, electrons, heavy ions, and the like, for example.

Furthermore, the terms "patients", "subjects" and "individuals": may be used interchangeably herein as they basically refer to an individual that is receiving radiation treatment from any of the MRI-linac systems described herein or is being imaged by any of the MRI systems described herein.

Furthermore, it should be noted that the radiation beam and/or the various forms of imaging described herein can be applied to an object which comprises an individual, a test subject, a patient, an animal specimen or a phantom.

It should be noted that terms of degree such as "substantially", "about" and "approximately" as used herein mean a reasonable amount of deviation of the modified term such that the end result is not significantly changed. These terms of degree should be construed as including a deviation of the modified term if this deviation would not negate the meaning of the term it modifies.

Furthermore, the recitation of any numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation up to a certain amount of the number to which reference is being made if the end result is not significantly changed.

Recently, the concept of integrating an MRI scanner with a therapy radiation source (e.g. a linac, a Co-60, etc.), emerged as a feasible novel approach for MRI-guided Radiation Therapy (MRIgRT). The two main configurations previously proposed consist of a) a coupled system consisting of either a linac head[2, 3] or multiple Co-60 sources[4, 5] rigidly attached to an MRI scanner (cylindrical bore[3] or bi-planar[2] type) via a rotating gantry, and b) a decoupled system consisting of a typical linac interacting with an MRI scanner on rails, which travels in and out of the treatment room and is capable of imaging in close proximity of the linac.[6, 7] All proposed MR-linac systems feature MR scanners with all magnet components being in a fixed and non-movable position relative to each other or relative to the imaging volume. Thus, conventionally, the MR magnets can generate a single and non-adaptive imaging volume (e.g. a sphere with a 40 cm diameter). Both MRIgRT systems can be used for daily MRI-based patient setup verification. However, only coupled MRIgRT systems are expected to be capable of real-time tracking of soft-tissue tumor motion during radiation treatment delivery.[4, 8, 9] The MRIgRT systems have the potential to significantly boost the ability to perform Adaptive Radiation Therapy (ART). ART endeavors to improve the treatment of each individual patient by considering the repeated optimization of the patient's treatment plan based on feedback from day-to-day image data regarding anatomical changes (i.e., the tumor's shape, size and location, for example).

The MRIgRT systems relying on the integration of a linac with an MRI scanner are known in the literature as MR-linac systems. For such a system, the integration of the MRI scanner and the linac is a challenging task due to the mutual interaction between the two integral components. To operate independently, as well as in unison, any feasible MR-linac design addresses certain technical challenges, specifically: a) magnetic field interference,[10, 11] b) Radio Frequency (RF) interference[12, 13] and c) dose deposition effects in the external magnetic field of the MRI scanner.[14-17] In addition, skin dose effects caused by electron contamination,[18, 19] which are electrons that are produced in the linac head as well as in the air along the radiation beam path and then focused by the fringe field of the MRI scanner and directed towards the MR imaging volume, may also play an important role if they are not accounted for. Another design consideration includes avoiding the irradiation of MRI coils, which may introduce a spurious signal interfering with optimal operation for MR imaging.[20-22] Furthermore, the irradiation of the MRI coils may lead in time to radiation damage of sub-components, which may affect the overall performance of the imaging system.

The magnetic field interference refers to the MRI scanner's magnetic field induced effects on the optimal operation of the linac. Specifically, the presence of a sufficiently strong external magnetic field may perturb the trajectories of the electrons that are produced by the linac's gun and accelerated through the waveguide system towards the x-ray target.[3, 11, 23, 24] Thus, the linac waveguide and the gun are sufficiently shielded against the MRI scanner fringe field to ensure that the behavior of the traveling electrons is unaltered. As is known by those skilled in the art, the magnetic fringe field can be minimized in the regions of interest by using at least one of: a) passive shielding by using metallic components (such as, but not limited to, steel or Mu-metal, for example),[2, 25] b) active shielding by means of specially designed coil configurations,[3] or c) a combination of a) and b).

The imaging performance of the MRI scanner is affected by the RF generated by the linac since various sub-systems of the linac, e.g. a klystron/magnetron and a high voltage modulator, can generate sufficient RF noise that would interfere with the operational frequencies employed in MR imaging. To overcome such an impediment, one or more design dependent techniques can be considered such as: a) the re-location of the main sources of RF noise in adjacent rooms, b) the synchronization of the linac RF-signal triggering and pulse shaping (e.g. each pulse is 7 μs in duration with a frequency of 50 pulses/s) with the MR's RF image sequence readout (e.g. for a gradient echo sequence the pulse is less than 1 ms in duration and the pulse frequency is 100 pulses/s), and c) the use of a Faraday cage (i.e. a fine mesh of copper) to RF shield the linac waveguide.

The dosimetric effects refer to the change in the local behavior of the secondary charged particles generated in a medium by radiation (e.g., X-ray) due to the presence of an externally applied magnetic field (i.e. the magnetic field ($B_0$) of the MR scanner).[14, 15, 17, 26] As a consequence, the dose deposition patterns in the medium are significantly modified as compared to the case where there is no magnetic field. The dosimetric effects are due to the presence of a Lorentz force: $F=q \cdot v \times B_0$, where F is the force experienced by a charge (q) travelling with a certain velocity (v) in an external magnetic field ($B_0$). Specifically, the trajectories of the electrons between subsequent collisions are modified (i.e. helical trajectory) depending on the electrons' kinetic energy and the strength of the magnetic field ($B_0$). In particular, the magnitude of this effect is enhanced at the interface of high-to-low electron density materials. For example, in the case of a tissue-air interface, the exit electrons travel a longer path in air than in tissue and can curl back and return into the tissue under the influence of an external magnetic field.[17, 27] As a consequence, the tissue exit dose may increase compared to the case where there is no magnetic field. Accordingly, the magnitude of the dosimetric effect is dependent on the strength of the magnetic field, the electron velocities and the sample geometry. The dosimetric effects are reduced to some extent when the radiation beam is oriented in-line relative to the magnetic field ($B_0$) rather than being orthogonal.[15] In this case, the travelling electrons tend to be re-focused along the direction of the treatment beam.

The various embodiments described herein generally relate to a Radio-Therapy (RT) system and an associated method, and in particular to an integrated radiation source with an MRI system featuring magnets that are independently moveable with respect to the radiation source and the patient. Accordingly, instead of moving the patient to obtain images of different regions of interest (e.g. volumes) of the patient, as is conventionally done, the magnets of the various embodiments described herein may be moved to various positions with respect to the patient and the radiation source which allows for increased imaging and treatment flexibility. The use of an MRI system with moveable magnets also allows for a reduced and adjustable imaging Field Of View (FOV) that can be tailored for various RT specific applications such as, but not limited to, at least one of patient setup verification and real-time tumor tracking, for example.

Generation of the Main Magnetic Field: General Concepts and Configurations

Figure 1B:
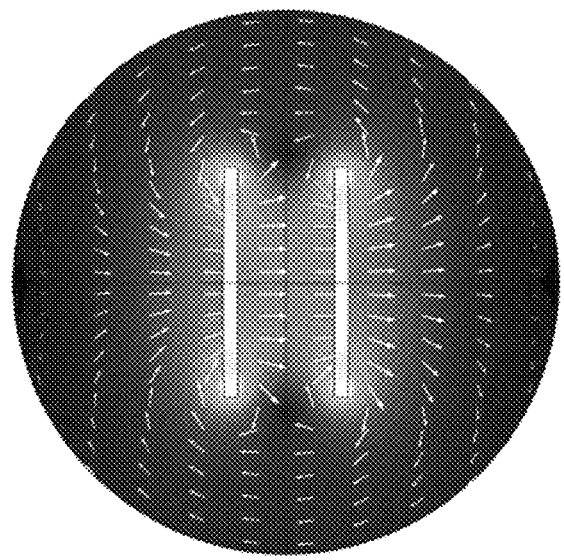
Figure 1C:
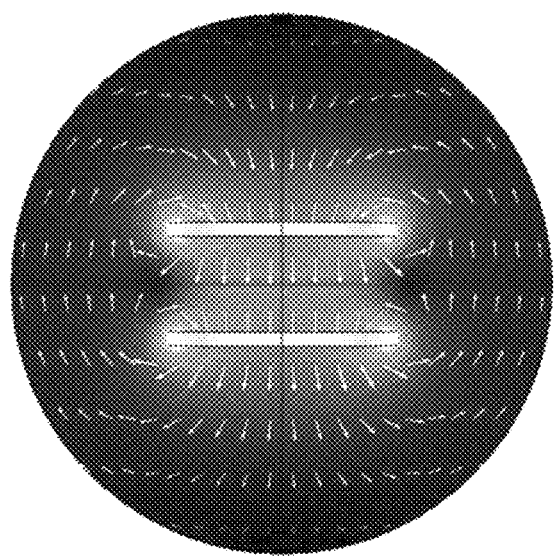

Referring now to FIGS. 1A-1C, shown therein are perspective, (x,y)-plane and (y,z)-plane views, respectively, of the spatial distribution of a Magnetic field ($B_0$) that is generated by an arbitrary coil pair. In particular, FIG. 1A shows a 3D view of the coils (in grey) and the corresponding Magnetic field ($B_0$) in two orthogonal planes.

The magnetic field ($B_0$) can be time-independent. In FIGS. 1A-1C, the magnetic field lines are depicted by the white arrows, which run parallel to each other in the uniform field regions and diverge as the local field inhomogeneity increases. The spatial distribution of the magnetic field ($B_0$) is modified by adjusting parameters such as the coil radii and spatial location as well as the current and direction of the various coils. This concept can be extended to build complex geometries. Considering the coil pair as being a unit cell, MR magnets (that are resistive and superconductive) can be designed to generate arbitrarily shaped homogeneous or inhomogeneous magnetic field distributions (this design can be done by using numerical simulations that use linear programming techniques and optimization methods).[28-31] In this approach, through several iterations, a coil space is sampled to search for a global solution corresponding to the most optimal ensemble of coils. The optimized coil configuration includes the generation of the MR coil's main magnetic field as well as active shielding, which is required to limit the extent of the fringe fields beyond the MR coils' structure. In at least one embodiment, the optimization process may be performed to also minimize the power dissipated by the MR magnet coils, the coil volume, the conductor mass and/or its physical footprint.

Figure 2A:
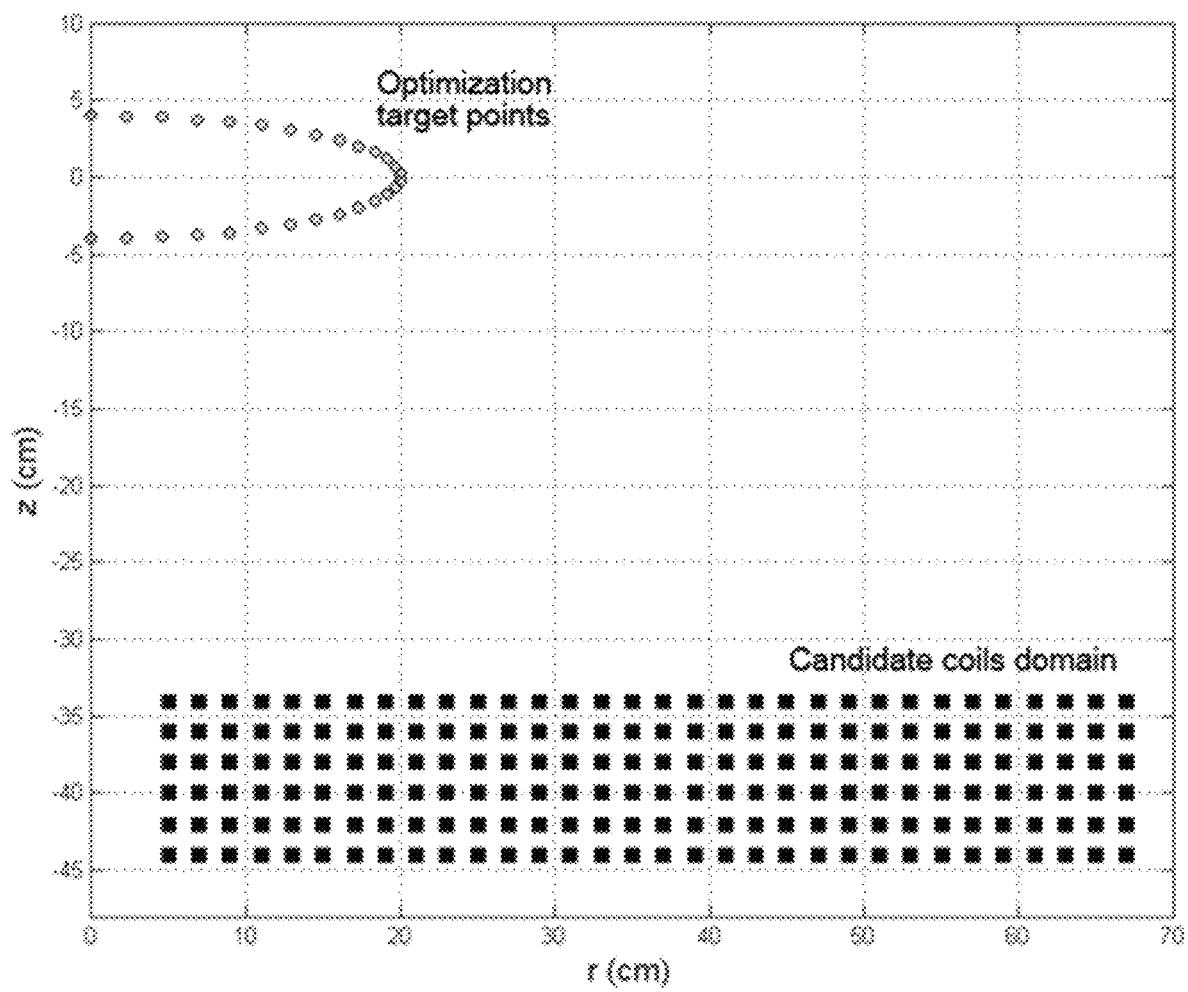
FIG. 2A shows an example embodiment of an MR magnet optimization environment for a monopole MR magnet configuration that may be used with an MR-linac system in accordance with the teachings herein.
Figure 2B:
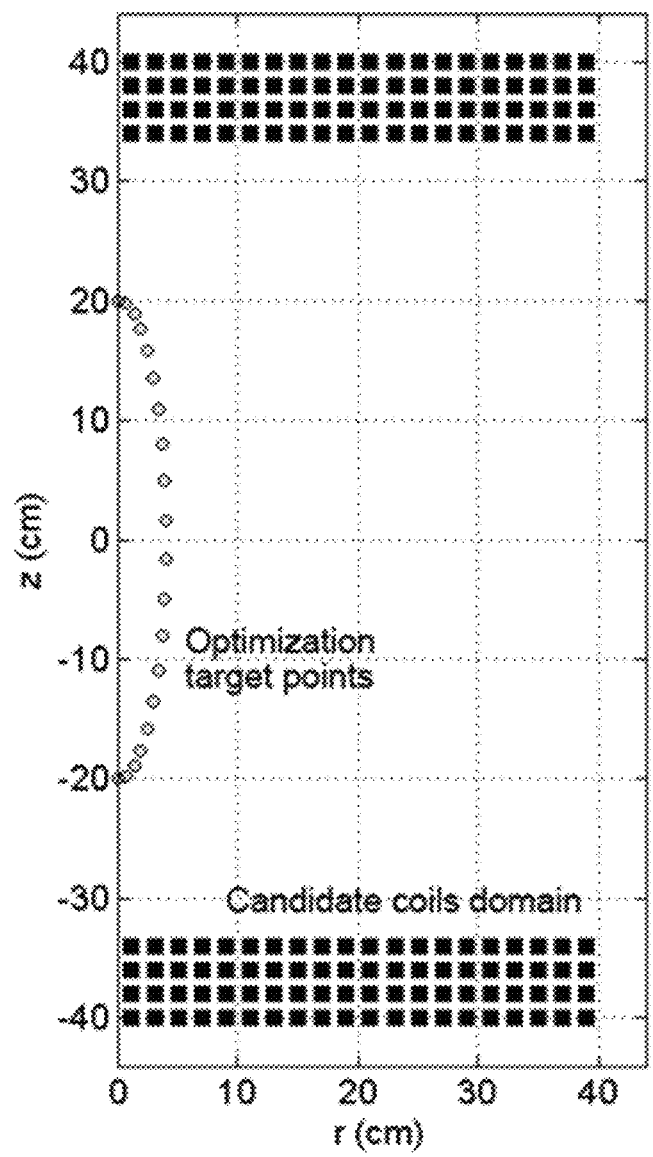
FIG. 2B shows an example embodiment of a candidate coils domain for a biplanar MR magnet configuration that may be used with an MR-linac system in accordance with the teachings herein.
Figure 2C:
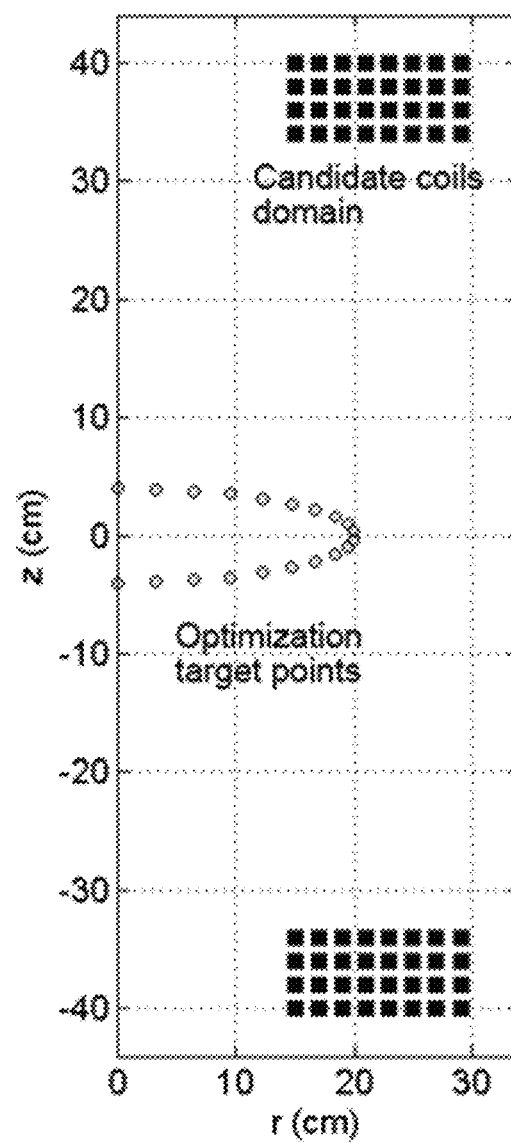
FIG. 2C shows another example embodiment of a candidate coils domain for a biplanar MR magnet configuration that may be used with an MR-linac system in accordance with the teachings herein.

The concept of candidate coils is shown in FIGS. 2A-2C. Due to axial symmetry, only half of the magnet space is depicted, using a cylindrical system of coordinates. The candidate coil locations of an MR magnet may be defined for any arbitrary imaging volume (e.g. a sphere, an ellipsoid, a cylinder, etc.). Each square marker represents the cross-section center of a candidate coil, and the coils revolve around the z-axis. The square markers do not represent the dimensions or the cross-sections of the coils, but rather points located at the center of ideal current filaments, which can be translated into realistic coils. The circular markers represent the optimization target points on the surface of the MR imaging volume. These target points are used in the optimization process to set a certain homogeneity tolerance for the MR imaging volume (e.g. 10 parts per million or ppm).

In the examples shown in FIGS. 2A-2C the imaging target volume is given by an ellipsoid with the main axes being 40 cm (z and x-axes) and 8 cm (y-axis). The coil domain is chosen in such a way that several constrains are fulfilled: i) enough patient clearance (i.e. the distance from coils to the MR isocenter should be large enough to fit a patient and a treatment/imaging table), ii) sufficient separation to allow for additional structures used for the operation of the MR such as the cryostat, gradient/RF/shim coils, etc., iii) sufficient clearance to rotate the magnet component(s) around the patient, iv) dimension of the entire coil ensemble (i.e. lateral and depth extent of the candidate coil domain), and v) achievement of realistic currents for an optimized coil configuration.

For a monopole MR magnet that can be used in a MR-linac system, an example embodiment of the candidate coil domain, in other words the MR magnet optimization environment, is shown in FIG. 2A. In this case, the imaging volume corresponds to an ellipsoid, and the in-plane cross-section is an ellipse. The candidate coil locations are located only on one side of the ellipsoid imaging volume, which is defined by the optimization target points.

In FIGS. 2A-2C, the MR imaging volume is defined by an ellipsoid oriented with the larger axes (x,z)-plane in the BEV of the linac.

FIG. 2B shows an example embodiment of the candidate coils domain for a biplanar MR magnet. In particular, FIG. 2B corresponds to the MR-linac configuration with the MR magnetic field orthogonal to the linac radiation beam (delivered from the left/right). The coils domain has a top and bottom component to depict the two opposed magnet poles. The target imaging volume is an ellipsoid with the larger axis along the z-axis. This MR configuration may be integrated with a linac head, which would deliver the radiation beam in the horizontal plane (e.g. from left to right). This means that the ellipsoid has the large circular cross-section (e.g. 40 cm diameter) in the BEV of the linac beam or the coronal plane of the patient.

FIG. 2C shows another example embodiment of the candidate coils domain for a biplanar MR magnet. In particular, FIG. 2C refers to an MR-linac configuration where the MR magnetic field is oriented in-line with the linac radiation beam. The candidate coils domain has a top and bottom component to depict the two opposed magnet poles. Accordingly, in this case, the linac beam is delivered from top to bottom or vice-versa, through the open space at the coils of the MR magnet. Furthermore, the candidate coifs domain in FIG. 2C has a smaller lateral extent to allow for a coil opening which can be utilized to deliver the linac beam. The target imaging volume is an ellipsoid with the larger axis orthogonal to the z-axis. To achieve the configuration shown in FIG. 2C, the candidate coil domain is not available in the close vicinity of the z-axis. Thus, only coils with larger radii are allowed to contribute to the magnetic field at the imaging target points.

The magnetic field at any target point is given by the superposition of the fields generated by all the coils. In matrix form, this is given by $$B = A*I \quad (1)$$

The j-th coil, with radius $r_j$ and location $z_j$ along the z-axis, contributes to the i-th target point given by $R_i$ and $Z_i$ with a field described by the following equations[32]:

$$A_{ij}^z = \frac{\mu}{2\pi} \left[ \frac{1}{(R_i + r_j)^2 + (Z_i - z_j)^2} \right]^{1/2} \times \left[ K(k_{ij}) + E(k_{ij}) * \frac{r_j^2 - R_i^2 - (Z_i - z_j)^2}{(R_i - r_j)^2 + (Z_i - z_j)^2} \right] \quad (2)$$

$$A_{ij}^\rho = \frac{\mu}{2\pi r_j} \left[ \frac{z_j}{(R_i + r_j)^2 + (Z_i - z_j)^2} \right]^{1/2} \times \left[ -K(k_{ij}) + E(k_{ij}) * \frac{r_j^2 + R_i^2 - (Z_i - z_j)^2}{(R_i - r_j)^2 + (Z_i - z_j)^2} \right] \quad (3)$$

where $A_{ij}^z$ and $A_{ij}^\rho$ are the z-axis and radial components of the magnetic vector potential, respectively. The coefficient $k_{ij}$ is given by:

$$k_{ij} = \left[ \frac{4 R_i r_j}{(R_i + r_j)^2 + (Z_i - z_j)^2} \right]^{1/2} \quad (4)$$

K and E represent elliptical integrals of the first and second kind, namely:

$$K(k_{ij}) = \int_0^{\pi/2} \frac{d\theta}{\sqrt{1 - k^2 \sin^2 \theta}} \quad (5)$$

$$E(k_{ij}) = \int_0^{\pi/2} \sqrt{1 - k^2 \sin^2 \theta} \, d\theta \quad (6)$$

To generate an arbitrary coil configuration, an optimization problem can be solved considering Equation 1.[28] The coil configuration is optimized by considering the power dissipated by the coils, the total volume of the coils, the coif conductor mass and/or coil ensemble physical footprint. For example, the volume of the coils is given by:

$$V_{coils} = \frac{2\pi}{J_c} \Sigma_{j=1}^N r_j I_j \quad (7)$$

where $J_c$ is the current density, and N is the total number of coils. The optimization problem may be defined as follows[28]:

Minimize: $\Sigma_{j=1}^N r_j I_j$

Subject to: $A*I \leq B_0(1+\varepsilon)$ $$-A*I \leq -B_0(1-\varepsilon) \quad (8)$$

$|I_j| \leq t_j, j = \overline{1,N}$ where $B_0$ is the strength of the MR magnetic field, $\varepsilon$ is the field homogeneity tolerance factor for $B_0$ (e.g. 10 ppm), and t is a vector that is used to simplify the optimization problem. Equations 8 represent a linear optimization problem which may be solved by using numerical methods.

It should be noted that the locations of the movably adjustable magnet components (e.g. coils) are constrained by the candidate coils domain in the optimization problem. One can define any arbitrary spatial distribution of the magnet components (translation and rotation) for which the optimization algorithm will solve to generate realistic solutions. Therefore, theoretically, a solution can be reached given a desired magnet configuration with an arbitrary large/small separation or travel of the movably adjustable magnet components. The separation or travel of the magnet components is custom to the targeted MR applications and desired imaging volumes, e.g. large for pelvis patients, small for head/neck patients.

For a pre-defined imaging target volume and a candidate coil domain, the optimization is performed to generate the best coil configuration which minimizes the optimization objectives. In the case of a monopole magnet configuration (e.g. FIG. 2A), bi-planar magnet configuration (e.g. FIGS. 2B and 2C), or a solenoid magnet configuration, the magnetic field used for optimization is given by the z-component, see Equation (2). This assumption is valid as the radial component is negligible. However, for a magnet configuration with multiple non-coplanar magnet components (see FIGS. 7A-7C), the optimization may be performed considering both magnetic field components as per Equations 2 and 3.

Figure 3:
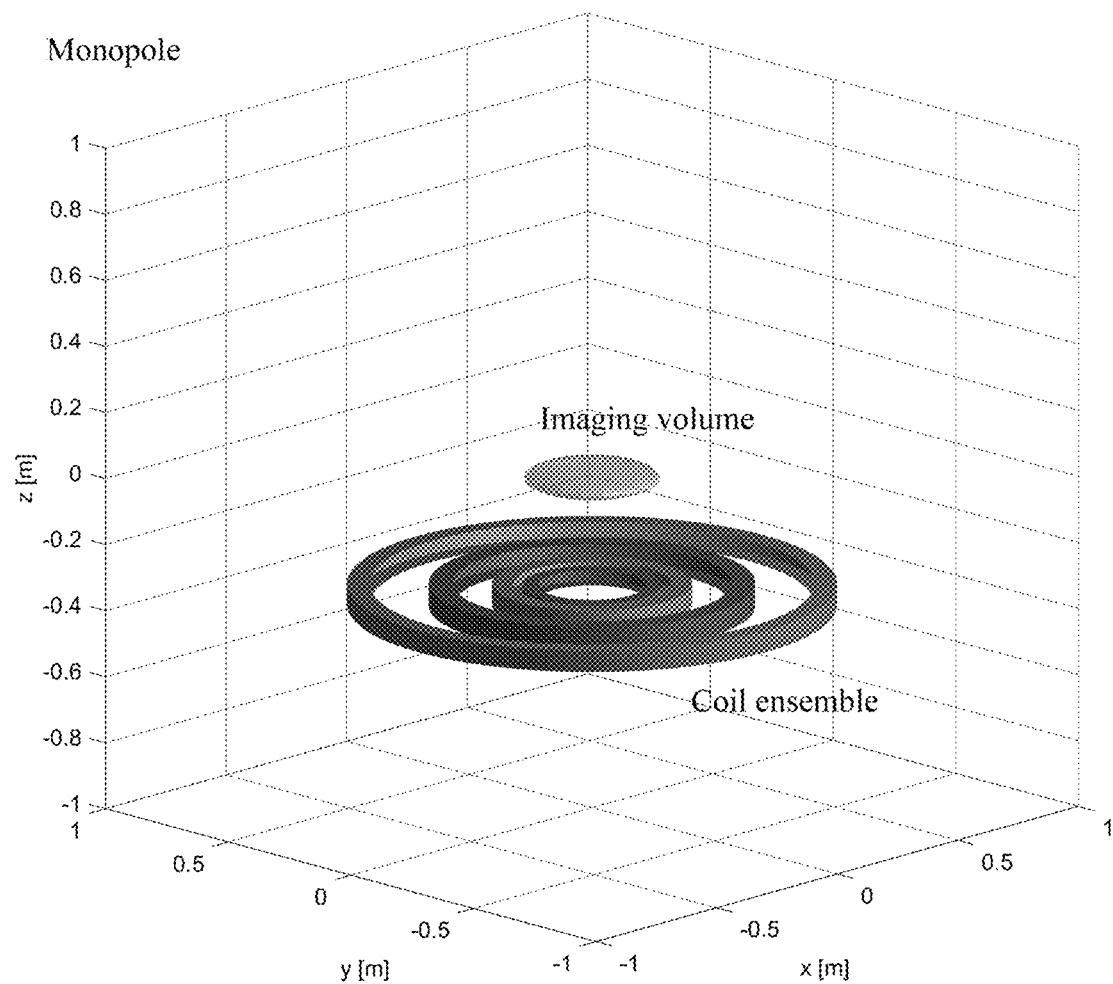
FIG. 3 shows an example embodiment of a monopole MR magnet configuration and an imaging volume that is derived from using the candidate coils domain presented in FIG. 2A.

Referring now to FIG. 3, shown therein is an example embodiment of a monopole MR magnet that is derived using the candidate coils domain presented in FIG. 2A. The coil specifications are summarized in Table 1. The imaging volume is an ellipsoid with a circular cross-section of 40 cm diameter in the (x,y)-plane and 8 cm axis along z-axis. This MR magnet configuration may be integrated with a linac in such a way that the monopole is mounted on a robotic arm to face the linac beam, and the ellipsoid imaging volume has the larger circular cross-section (e.g. 40 cm diameter) in the linac BEV. In this case, the magnetic field inside the ellipsoid imaging volume would be in-line with the direction of the linac radiation beam. In this case, four coils may be used to achieve a $B_0 = 0.4$ T with a field homogeneity tolerance of 100 ppm. The coil's color represents the direction of the current in the coil. Table 1 summarizes the characteristics of the coils.

TABLE 1

|        | r (cm) | z (cm) | I (kA)   |
|--------|--------|--------|----------|
| Coil 1 | 18     | 34     | −1225.2  |
| Coil 2 | 26     | 34     | 2200.1   |
| Coil 3 | 44     | 34     | −2756.0  |
| Coil 4 | 68     | 34     | 2414.2   |

An example embodiment that may use the coil configuration of FIG. 3 is an MRIgRT system that integrates a radiation source (i.e. a linac, a Co-60, a proton source and the like) with an MRI scanner. This example system will be referred to as MR-linac system 1 and has the following features:

1a) The magnetic field ($B_0$) of the MRI scanner may feature a single magnet pole (i.e. monopole), consisting of at least one magnet component. The monopole may be a permanent magnet, an electromagnet, a superconductor, or a combination of any of these magnets. The monopole may be mounted via a robotic arm on a typical linac gantry to replace the megavoltage (MV) panel detector of the linac, for example. For a typical linac, the MV detector is mounted opposite to the linac head and faces the radiation beam. In this configuration, the monopole may be moved to pre-defined locations behind the patient that is laid on the treatment table to perform MR imaging. The monopole's imaging volume may be defined by a reduced FOV in the coronal plane or the BEV of the linac beam, with a reduced slab magnetic field ($B_0$) at a central axis and in some cases the imaging plane is in the coronal plane of the patient being imaged. The monopole may rotate in unison with the linac gantry, similar to an MV panel detector, and perform snapshot or continuous (1D, 2D) MR imaging at any arbitrary gantry rotation angle.

1b) In some situations, the monopole may be integrated with the MV panel detector to provide both MR and MV imaging prior and during linac beam delivery.

1c) In the scenarios described in 1a and 1b, the kilovoltage (kV) capability of the linac, consisting of the KV x-ray source and panel detector, may be preserved. For 1a the linac may provide dual imaging from the MRI and the kV and for 1 b the linac may provide three on-board imaging modalities, specifically, MRI, kV and MV.

Figure 4A:
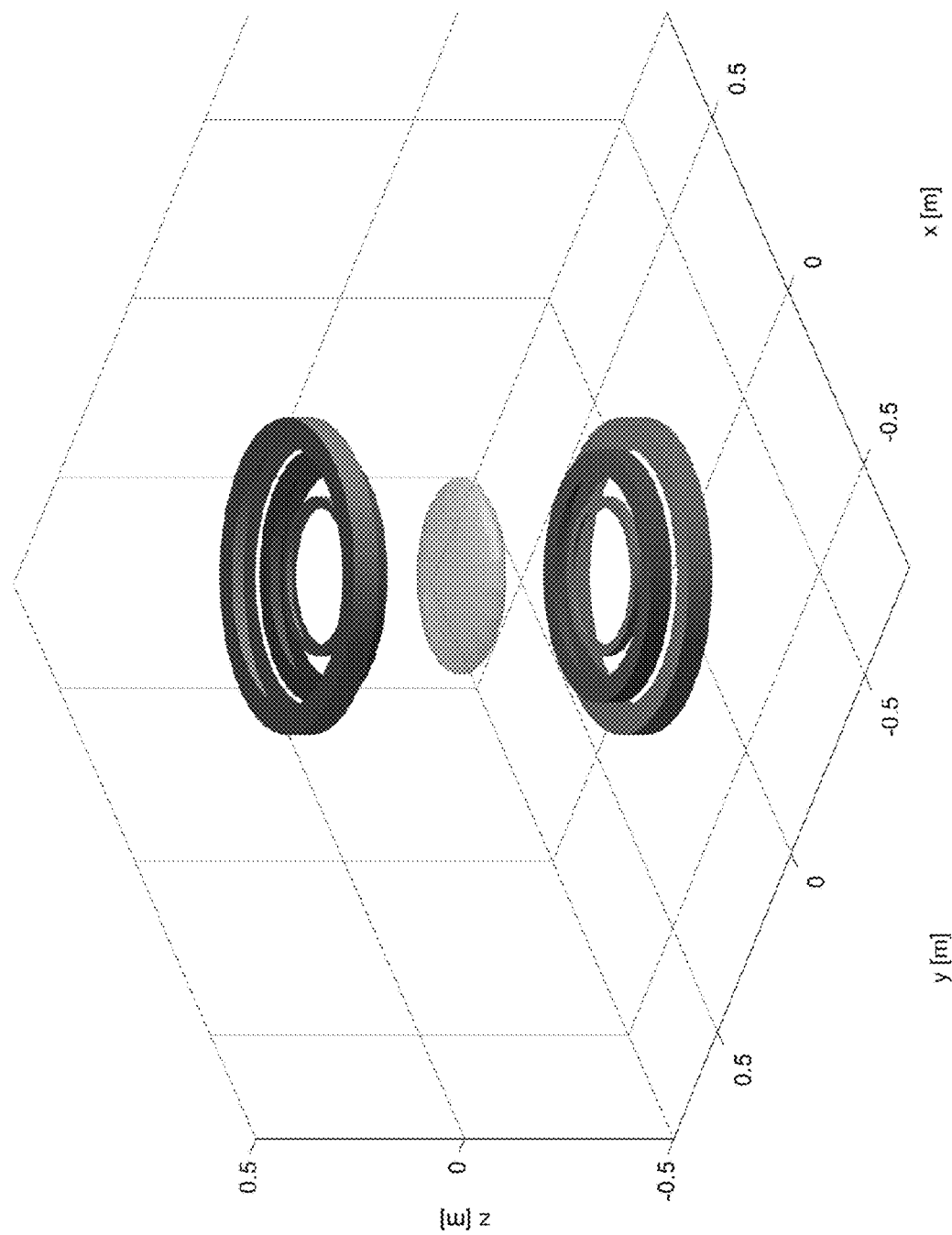
FIG. 4A shows an example embodiment of a first biplanar MR magnet configuration and an imaging volume that is derived from using the candidate coils domain presented in FIG. 2C.
Figure 4B:
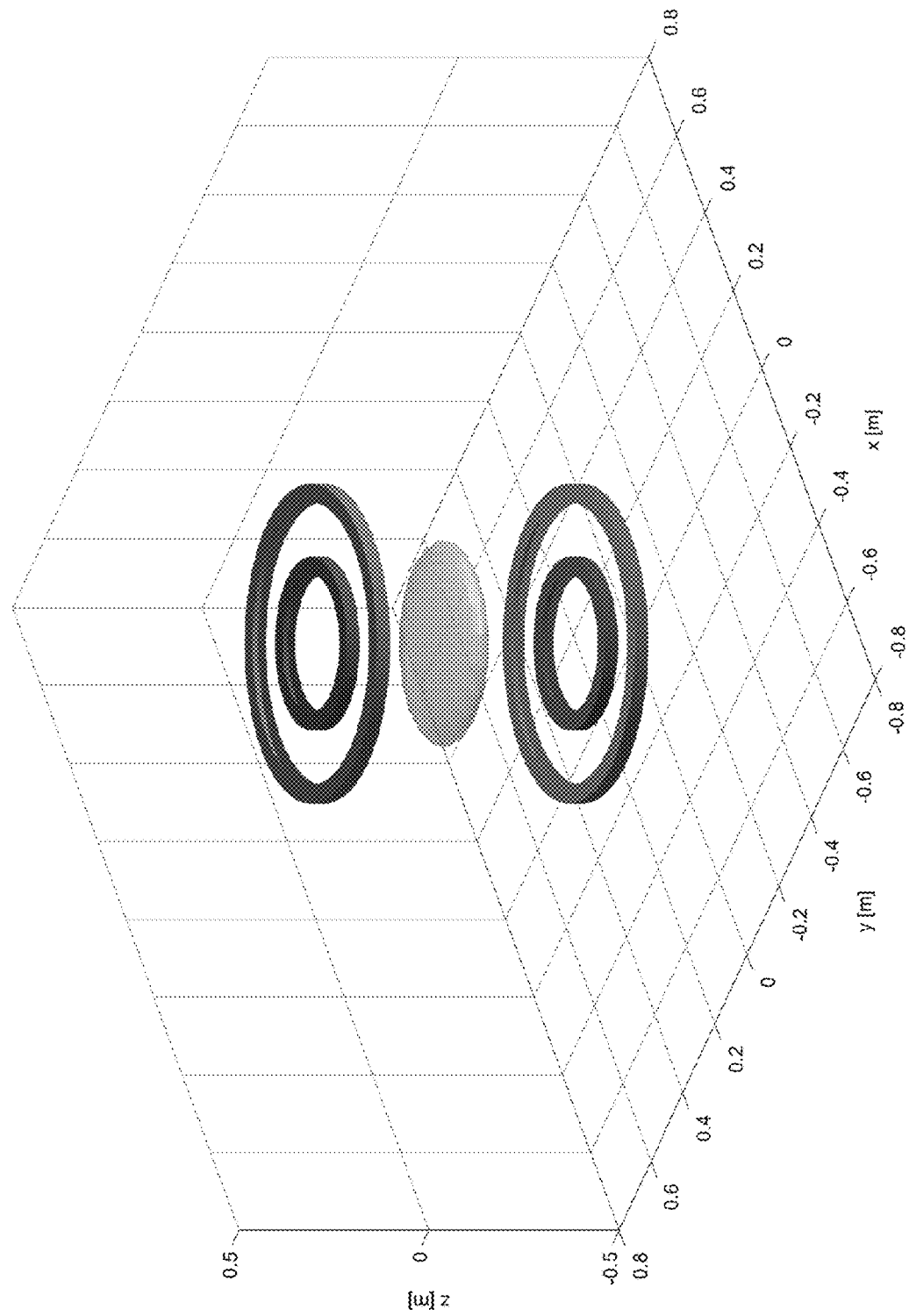
FIG. 4B shows an example embodiment of a second biplanar MR magnet configuration and an imaging volume that is derived from using the candidate coils domain presented in FIG. 2C.

FIGS. 4A-4B show example embodiments of two biplanar MR magnet (i.e. coil) configurations with different optimization targets that are derived using the candidate coils domain presented in FIG. 2C. The same target imaging volume was assumed as in FIG. 3. The coil configurations in FIGS. 4A and 4B were generated for $B_0$=0.5 T and a field homogeneity tolerance of 10 ppm and 100 ppm, respectively. The coil configurations correspond to an MR-linac with the beam and $B_0$ being parallel to each other and the radiation beam is oriented along the z-axis. In both configurations, increasing the field homogeneity results in coil requirements that become more demanding, i.e. higher coil currents.

For the biplanar MR magnet configuration of FIG. 4A, the coil specifications are summarized in Table 2. This MR configuration can be integrated with a linac, which would deliver the radiation beam along the z-axis (e.g. from top to bottom). This means that the ellipsoid has the large circular cross-section (e.g. 40 cm diameter) in the BEV of the linac beam (or the coronal plane of the patient at 0° gantry angle rotation). In this case, the magnetic field inside the ellipsoid imaging volume is in-line with the direction of the linac radiation beam.

TABLE 2

|        | r (cm) | z (cm) | I (kA)   |
|--------|--------|--------|----------|
| Coil 1 | 15     | 34     | 264.9    |
| Coil 2 | 23     | 34     | −1366.2  |
| Coil 3 | 29     | 40     | 1902.4   |

For the biplanar MR magnet configuration of FIG. 4B, the coil specifications are summarized in Table 3. Similar to the configuration of FIG. 4A, the magnetic field inside the ellipsoid imaging volume is in-line with the direction of the linac radiation beam.

TABLE 3

|        | r (cm) | z (cm) | I (kA)   |
|--------|--------|--------|----------|
| Coil 1 | 15     | 34     | −674.45  |
| Coil 2 | 29     | 34     | 735.75   |

Figure 5:
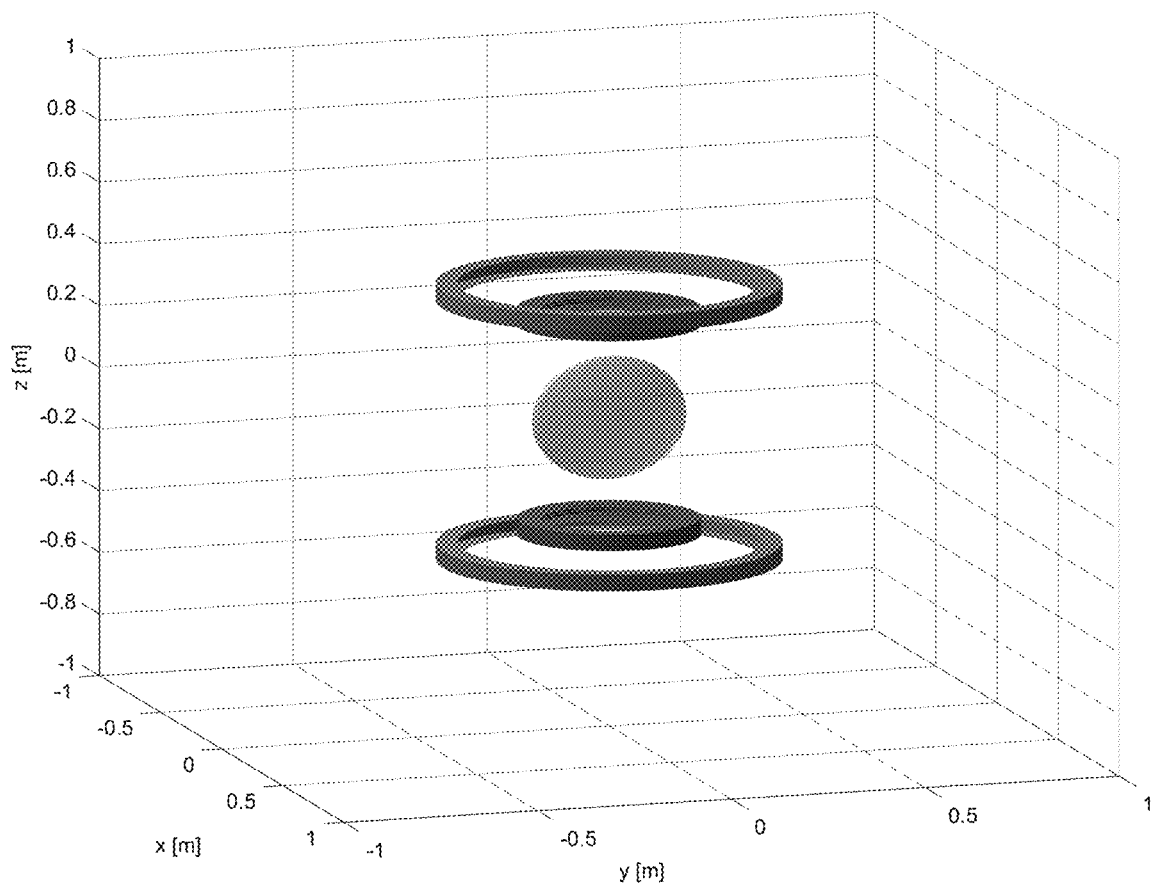
FIG. 5 shows an example embodiment of a third biplanar MR magnet configuration and an imaging volume that is derived from using the candidate coils domain presented in FIG. 2B.

Referring now to FIG. 5, shown therein is an example embodiment of a biplanar MR magnet configuration that is derived using the candidate coils domain presented in FIG. 2B. The coil ensemble of FIG. 5 was optimized to generate a uniform field within an ellipsoid with a circular cross-section in the (y,z)-plane with a diameter of 40 cm and an elliptical cross-section in the (x,z)-plane with the smaller axis of 8 cm. The optimization criterion also included achieving a homogeneous ellipsoid imaging volume with a tolerance of 100 ppm. The MR magnet configuration of FIG. 5 can be integrated with a linac, which would deliver the radiation beam orthogonal to the z-axis. This means that the ellipsoid has the large circular cross-section (e.g. 40 cm diameter) in the BEV of the linac beam (or the coronal plane of the patient at 0° gantry angle rotation). In this case, the magnetic field inside the ellipsoid imaging volume is orthogonal to the direction of the linac radiation beam. The linac beam is oriented along the x-axis.

Similar to the MR magnetic configurations shown in FIGS. 4A, 4B and 5, more complex MR magnets can be designed. For example, the coil configurations for the MR scanner described with respect to FIGS. 7A-7C may be defined as in FIGS. 6A and 6B for the in-line and orthogonal MR-linac configurations, respectively.

Figure 6B:
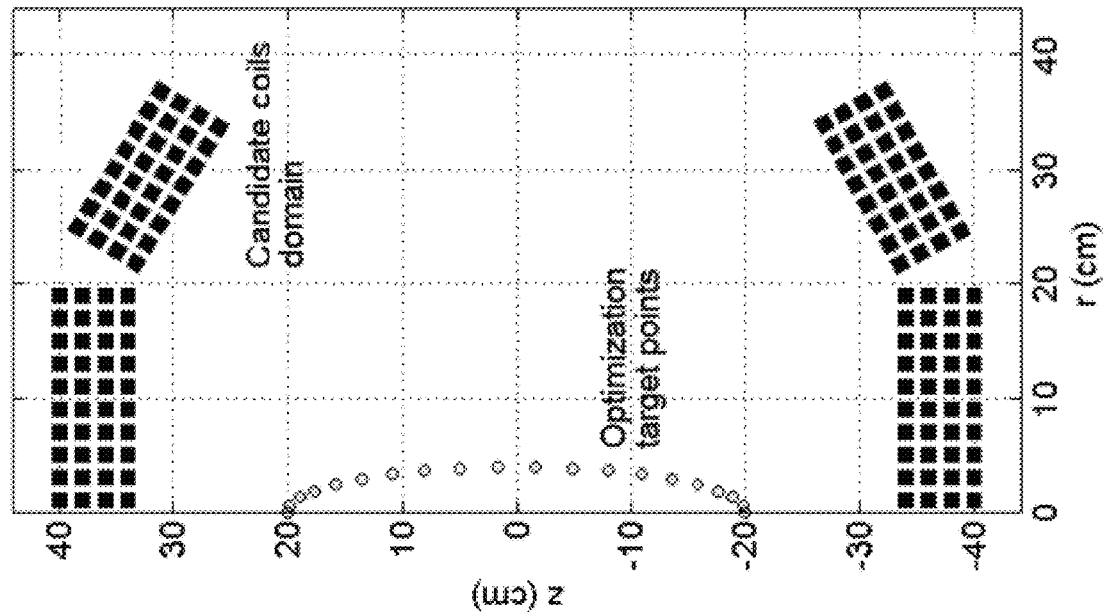
FIG. 6B shows an example embodiment of an MR magnet optimization environment for a complex MR with multiple non-coplanar magnet poles.
Figure 6A:
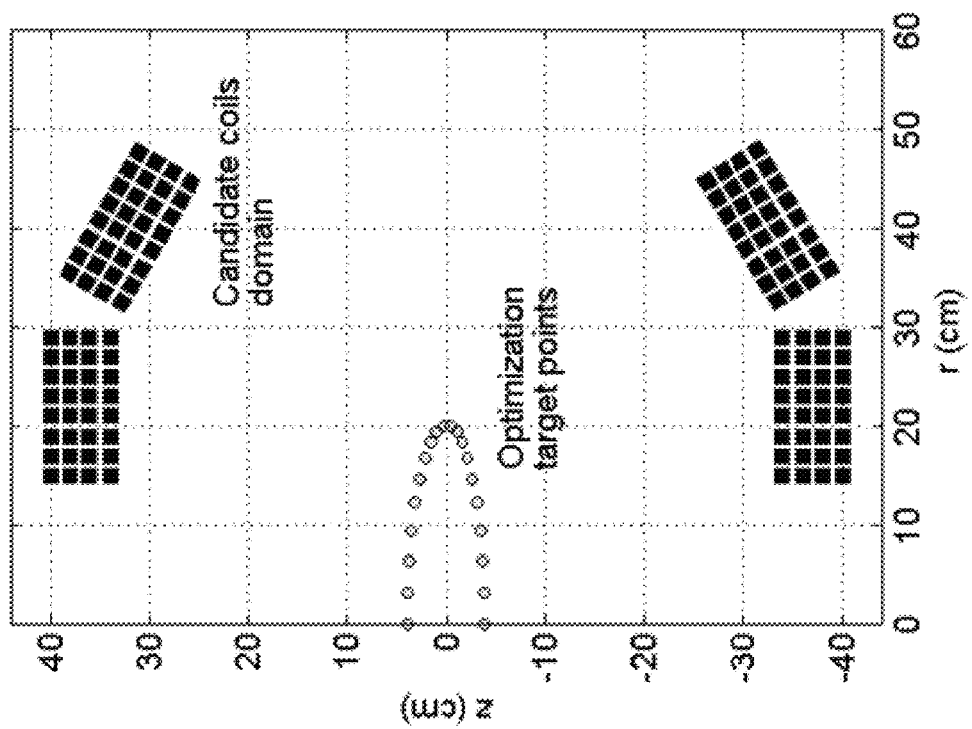
FIG. 6A shows an example embodiment of an MR magnet optimization environment for a complex MR with multiple non-coplanar magnet poles.

FIG. 6A shows the MR magnet optimization environment for an example embodiment of a complex MR with multiple non-coplanar magnet poles. Due to axial symmetry only half of the magnet space is shown. The square markers represent the location of the candidate coils. The circular markers represent the optimization target points on the surface of the MR imaging volume. The shape of the imaging volume can be arbitrary. In this case, the volume corresponds to an ellipsoid, and the cross-section is an ellipse. The candidate coils domain was chosen to generate a magnet with a magnetic field in-line with the linac radiation beam. The concept is similar to FIGS. 2C and 4A-4B. By modifying the location of the non-coplanar coils domain multiple imaging volumes can be generated.

FIG. 6B shows the MR magnet optimization environment for an example embodiment of a complex MR with multiple non-coplanar magnet poles. The schematic is similar to FIG.

6A, however, the magnetic field is orthogonal to the direction of the linac beam. The imaging ellipsoid is set in the coronal plane of the patient, or the linac BEV. The candidate coils domain may also be used to generate realistic MR magnet configurations for the example embodiments shown in FIGS. 7A-7C.

For the integration of a linac with a reduced FOV MRI scanner, the magnetic field ($B_0$) may be generated by a structure having at least one magnet component that is strategically placed in the proximity of the patient anatomy that is exposed to radiation from the linac radiation beam during the treatment delivery. The magnetic field ($B_0$) partly or fully encompasses the irradiated volume for imaging purposes.

Referring now to FIGS. 7A-7C, shown therein are various views of an example embodiment of an MR-linac system 10 in accordance with the teachings described herein. This example embodiment shows the integration of MR magnet components with a typical L-shaped linac configuration to achieve the MR-linac system 10. Multiple magnet components are mounted on the linac's robotic arms at 90° with respect to the direction of the linac beam. Using the analogy with a typical linac, in at least one example embodiment, the MR magnet components would replace the kilovoltage source and panel detector. The robotic arms can be adjusted repeatedly, in a reproducible manner, to achieve certain pre-defined magnetic field ($B_0$) spatial distribution(s).

Referring now to FIG. 7A, shown therein are the main components of the MR-linac system 10 including an MRI scanner 12 and a linac 14. The MRI scanner 12 comprises a first set of magnets 12 having magnet components 12a, 12b and 12c and a second set of magnets 12' having magnet components 12a', 12b' and 12c'. At least some of the magnet components 12a, 12b, 12c, 12a', 12b' and 12c' may be adjustable for placement at a desired location or angle with respect to the patient. The linac 14 comprises a linac head 14a and a gantry 14b. The MRI scanner 12 is mounted to the linac 14 by robotic arms 16a and 16b. The MR-linac system 10 also includes a treatment table 18a having a table top 18b upon which a patient is positioned in order to receive a treatment or radiation beam 20 from the linac head 14a.

FIG. 7B is a front view of the MR-linac system 10 depicting a configuration in which the MR magnet components 12a-12c' (i.e. MR elements) are adjusted to be in close proximity to the portion of the patient that receives the radiation beam 20 and to allow for the generation of a larger imaging FOV. In this example embodiment, the MR components comprise top magnet components 12a and 12a', side magnet components 12b and 12b' and bottom magnet components 12c and 12c', at least some of which are moveable so that they have an adjustable position relative to the patient. For example in some embodiments, the top and bottom magnet components 12a, 12a', 12c, and 12c' may be movable while the center magnet components 12b and 12b' may be stationary in the proximity of the imaging volume. In another embodiment, the center magnet components 12b and 12b' may also be movable, for example, the center magnet components 12b and 12b' may be parked or moved away from the patient if MR imaging is not required for a particular patient of treatment session. In other words, all magnet components 12a to 12c' may be parked away from the patient in a retracted position of the robotic arms. In other embodiments, other combinations of magnet components may be used such as just top and bottom magnet components, top and center magnet components or bottom and center magnet components, in which at least some of the magnet components have an adjustable position.

FIG. 7C shows a front view of the MR-linac system depicting the top and bottom MR components 12a, 12a', 12c and 12c' in a retracted position in which case the imaging is performed with only the center magnet components 12b and 12b', which may be used to track target/organ motion during radiation treatment delivery.

The relative orientation of the magnetic field ($B_0$) with regard to the direction of the linac radiation field may be either in-line (parallel) or orthogonal to each other for the homogeneous region of the magnetic field. For example, FIG. 5 shows a realistic coil configuration for an MR magnet with a reduced imaging FOV, in the shape of an ellipsoid (see FIG. 4B and the associated description). The larger cross-section of the ellipsoid is in the BEV of the linac treatment beam, and the MR poles (i.e. center magnet components 12b and 12b') are mounted on robotic arms similar to the embodiment shown in FIGS. 7A-7C. In this configuration, the magnetic field is orthogonal to the direction of the linac treatment beam. This system will be referred to as MR-linac system 2. In another embodiment, additional magnet components may be added to resemble the top and bottom magnet components shown in FIGS. 6A-6B (i.e. non-coplanar candidate coils space). For this configuration, the capability of a linac's x-ray megavoltage (MV) panel detector may be preserved, as the panel is mounted to face the linac treatment beam. Thus, this example embodiment of an MR-linac system may allow dual imaging: MRI and x-ray MV.

In another example embodiment, the MR magnet configuration from FIGS. 4A-4B may be mounted on the linac gantry 14b, but this time the magnet poles are mounted such that the magnetic field is oriented in-line with the linac treatment beam. This system will be referred to as MR-linac system 3. One magnet pole of the MR magnet configuration may be mounted on the linac head 14a and the opposite magnet pole of the MR magnet configuration may be mounted on an additional robotic arm (not shown in FIGS. 7A-7C), located opposite to the linac head, to replace the linac MV panel detector. Thus, the linac treatment beam 20 passes through the opening of one of the magnet poles, i.e. the opening of the circular coil ensemble at the central axis or from top to bottom in FIGS. 4A-4B. Similar to FIG. 5, the ellipsoid imaging volume is in the BEV of the linac treatment beam. Similar to FIGS. 6A-6B and 7A-7B, the top and bottom magnet components may be added to generate multiple MR imaging regions. Considering that the magnet components are mounted such that the magnetic field in the imaging volume is oriented in-line to the linac treatment beam, for this particular example configuration, the capability for kV imaging may be preserved, for which the kV source (KVS) and kV panel detector (KVD) are mounted on additional robotic arms and oriented at 90° with respect to the direction of the linac treatment beam. Thus, this example embodiment of a MR-linac system may be used to provide dual imaging: MRI and x-ray kV.

In yet another example embodiment, a monopole magnet component (see FIG. 3 for example) may be mounted on a robotic arm, with the magnet pole facing the linac radiation beam and the ellipsoid imaging volume in the BEV of the linac. This system will be referred to as MR-linac system 4 which is a combination of MR-linac system 1 plus additional non-coplanar magnet components. The monopole magnet component may be moved to multiple locations behind the patient to perform imaging for i) patient setup verification prior to treatment or ii) real-time imaging (e.g. 1D, 2D) during linac rotation and radiation treatment delivery. In this example embodiment, additional non-coplanar magnet components may be added in the vicinity of the monopole to further shape the imaging volume or to house the imaging gradient and RF transmit/receive coils. For this example embodiment of the MR-linac system, the linac's x-ray KV imaging capabilities may be preserved. Thus, this MR-linac system may be used to provide dual MR) and x-ray kV imaging.

Another example embodiment comprises an MRIgRT system that integrates a radiation source (i.e. a linac, a Co-60, a proton source and the like) with an MRI scanner. This system will be referred to as MR-linac system 5 and has the following features:

2a. The MRI scanner may generate a main magnetic field ($B_0$) which is time-independent with an average spatial homogeneity across the entire imaging volume that is lower compared to the magnetic field ($B_0$) of a conventional MRI magnet.

2b. The magnetic field ($B_0$) of the MRI scanner may have two main imaging regions: i) a Region 1 having a reduced slab volume (e.g. a shape of an ellipsoid, cylinder) with a homogeneous magnetic field ($B_0$) at a central axis (in at least some embodiments, the imaging plane is in the coronal plane of the imaged patient) and ii) a Region 2 (e.g. a sphere, cylinder, ellipsoid, or arbitrary shape) that includes and extends beyond Region 1, with a magnetic field ($B_0$) homogeneity that gradually decreases with distance. The MRI scanner's Region 1 stays preferably orthogonal to the direction of the linac radiation beam at any gantry angle rotation. In other words, the slab imaging region is in the radiation beam's eye view (BEV) plane of the linac radiation field. This particular configuration facilitates 2D cine real-time MR imaging as well as 1D MR imaging during linac treatment beam delivery.

2c. The MRI scanner may feature only imaging Region 1 (i.e. in a single slice imaging operation mode) or both imaging Region 1 and Region 2.

2d. Regarding the homogeneous region of the magnetic field ($B_0$), the orientation of the magnetic field ($B_0$) relative to the direction of the linac radiation field may be either in-line or orthogonal. This means that the Lorentz force is either parallel or orthogonal to the direction of secondary electrons, which are generated when an x-ray interacts with the irradiated tissue (or material). The distinction between these two orientations is important as each orientation may lead to significantly different dose deposition patterns in the patient's tissue under the presence of the external magnetic field produced by the MR scanner. The use of the in-line or orthogonal orientation is also dictated by the configuration of the MR magnet components of the MRI scanner relative to the orientation of the linac treatment beam.

2e. The spatial distribution of the magnetic field ($B_0$) of the MRI scanner is adjustable by strategically modifying the location of certain MR components in the vicinity of the imaged patient or an imaged subject. As per feature 2b, the adjustment of the MR magnet components is performed by means of robotic parts (e.g. robotic arms), to enable two main modes of operation: i) in a first operation mode, certain magnet components are parked away from the patient (i.e. the patient's radiation treatment target or volume) and imaging is performed for Region 1 only (one purpose of this first operation mode is real-time imaging during treatment delivery), and ii) in a second operation mode, all magnet components are moved in the proximity of the subject, in a pre-defined and reproducible configuration, to generate larger imaging volumes, i.e. Region 2 (one purpose of this second operation mode is patient setup verification prior to each treatment fraction).

2f. The MR image reconstruction process relies on a combination of two methodologies: i) single slice reconstruction assuming a uniform magnetic field ($B_0$) for Region 1, and ii) image reconstruction assuming a non-uniform magnetic field ($B_0$) and prior knowledge of the spatial distribution of the field inhomogeneities (which can be measured experimentally, e.g. with a phantom or a linearity object) for Region 2.

2g. The MR magnet components and the linac are mechanically coupled on a common gantry, which allows for independent as well as in-unison imaging (MR) and radiation delivery (linac) at any rotation angle around the imaged patient (the center point of the gantry rotation coincides with both the MR magnet and linac isocenters).

Another example embodiment of an MRIgRT system integrates a radiation source (i.e. a linac, a Co-60, a proton source and the like) with an MRI scanner. The system will be referred to as MR-linac system 6 and has the following features:

3a. The magnetic field ($B_0$) of the MRI scanner may be highly homogeneous for a volume of interest, which can be varied by using movable magnet components (see FIGS. 7A and 7B).

3b. By moving the magnet components at different locations relative to each other and the patient, multiple imaging volumes (which may have different shapes, dimensions and spatial locations) may be generated. For example, a large imaging volume (e.g. a 40-50 cm sphere or any arbitrary shape) may be desired for a prostate patient, when the entire patient anatomy may be required for RT treatment planning, simulation and delivery. In another example, for breast imaging, the imaging volume that may be used may be smaller (e.g. a 20 cm sphere), and asymmetrically located with respect to the magnet components, to cover only the targeted breast anatomy, i.e. the imaging volume is moved closer to the magnet poles that are facing the targeted breast tissue.

3c. The magnet components may be non-coplanar in order to achieve at least one of small, large as well as asymmetric imaging volumes.

3d. The MV x-ray panel detector of the linac, mounted opposite to the linac head and facing the radiation beam, may also be present. In this configuration, the MR-linac system may provide dual imaging, i.e. MR and MV.

In at least one embodiment described herein, the MR magnet may be designed to be compact and used to deliver mainly radiotherapy specific functions such as imaging guidance for daily patient treatment setup verification and real-time acquisition during patient treatment delivery. The image quality should be sufficient to provide the spatial resolution, FOV coverage, signal sensitivity and temporal resolution (1D as in a navigator echo sequence and/or 2D as in a cine sequence) that are used for performing RT image guidance, but not necessarily comparable to the image quality of diagnostic MR. As a consequence, in this example embodiment, the MR-linac system may operate with only a few imaging sequences without the need for advanced modalities (e.g. MR spectroscopy).

At least one of the various MR-linac systems described herein may be configured to operate in a first operation mode with the magnet components in a certain position, as was shown in FIG. 7C in which the upper and lower magnet components 12a, 12a', 12c and 12c' are in a parked position in which they are moved further away from the patient. The central magnet components 12b and 12b' may then be used to generate a limited FOV homogeneous field (referred to herein as imaging in Region 1) that is sufficient to perform single-slice imaging or multiple-slice imaging in a reduced FOV that is orthogonal to the linac beam. For example, a single slice image in the patient's coronal plane at a 0° linac rotation (i.e. the BEV of the linac beam) may be obtained. An example embodiment of the operational workflow that may be used in this case is described with respect to FIG. 8B. The patient daily pre-treatment setup verification may be achieved by single slice imaging in two orthogonal planes (e.g. gantry angle 0° and 90°), without the need of the extra MR magnet components required to generate the imaging Region 2 (this is also referred to as the second mode of operation herein). During radiation treatment delivery 1D or 2D imaging may be performed to acquire, information for real-time visualization and tracking of tumor and adjacent organ motion. Considering the rigid coupling of the MR magnet components and the linac, as the gantry rotates, MR imaging may be continuously performed and data acquired at different cross-sections through the patient, which are always orthogonal to the radiation beam. Therefore, MR image data may be generated for the beam eye view (BEV) of the linac radiation field at any gantry rotation angle. The anatomical information retrieved in this plane, which is perpendicular to the linac beam during gantry rotation, may be the minimum amount of information that is used to image while providing radiation treatment. An oblique, or any other plane orientation, will use more anatomical information (i.e. more than one slice) to achieve the same goal.

For at least some of the various MR-linac systems described herein, the outer MR magnet components (for example, the upper and lower magnet components 12a, 12a', 12c and 12c' shown in FIG. 7A) may be retracted to minimize the exposure of the radiation sensitive MR components to the direct linac beam or scattered radiation. In an alternative embodiment, operating in the single slice mode, the MRI scanner may only have the central magnet components without the upper and lower magnet components and the central magnet components may be moveable closer to or farther away from the volume of the individual being imaged.

At least one of the various MR-linac systems described herein may be configured to operate in a second operation mode, in which the MRI scanner's imaging FOV may be extended by adjusting the position of the outer (e.g. upper and lower) MR magnet components, an example of which is shown in FIG. 7B, to generate a substantially larger imaging volume (referred to herein as imaging for Region 2). The resulting magnetic field ($B_0$) may feature a lower overall homogeneity across the imaging volume as compared to the magnetic field ($B_0$) of a conventional MR magnet. Beyond Region 1, the homogeneity of the magnetic field ($B_0$) in the imaging volume decreases with distance. The degree of inhomogeneities defines the extent of the usable imaging volume. An example embodiment of the workflow that may be used for this second operation mode is described with respect to FIG. 8E. For the second operation mode, the image reconstruction process may rely on a composite approach consisting of: a) using standard image generation methods assuming a uniform magnetic field ($B_0$) for the central slab FOV and b) using an algorithm for the case of an inhomogeneous magnetic field ($B_0$) (see below) which may be applied to regions located beyond the central slab FOV. A larger imaging FOV is desirable for the patient daily setup verification routine that is done prior to treatment delivery. However, one or two orthogonal slices may be enough to perform this task accurately.

In an example embodiment, there is provided a method for performing for performing at least one of radiation treatment, patient setup verification, real-time tracking of organ motion during radiation treatment delivery and MR imaging by using an MRI scanner and a radiation source (e.g. a linac). The MRI scanner has at least one magnet component that is moveable with respect to one of the linac and a desired imaging volume for an individual receiving radiation treatment. The method generally comprises performing patient setup for a treatment location with respect to the linac, adjusting the position of at least one moveable magnet of the MRI scanner, obtaining MR images and adjusting the patient setup based on the MR images, applying radiation treatment to the individual with simultaneous real-time MR imaging, and performing further MR imaging for post-treatment assessment of the individual.

It should be noted that real-time MR imaging using the various techniques described herein can be used for a variety of purposes including one or more of: 1. patient-setup verification prior to radiation treatment delivery to ensure that the patient is in the correct treatment position every day; 2. Real-time during radiation treatment (track organ motion to real-time drive and adjust treatment beam parameters); and 3. Post-treatment imaging to double-check that the patient did not move during delivery.

In another example embodiment, there is provided a method for performing MR imaging for a desired imaging volume of an individual using an MRI scanner having at least one moveable magnet. The method comprises determining the desired imaging volume for the individual, positioning the individual for imaging by the MRI scanner, adjusting at least one moveable magnet of the MRI scanner to position an actual imaging volume at the desired imaging volume and performing MR imaging of the individual.

In at least one embodiment, the MRI scanner comprises one adjustably moveable magnet component for providing an adjustable monopole with respect to a location of the individual.

In at least one embodiment, the MRI scanner comprises a pair of adjustably moveable central magnet components that are generally disposed across from one another on either side of the individual and the method comprises moving the adjustably moveable centrally magnet components closer to or farther away from the individual for MR imaging.

In at least one embodiment, the MRI scanner comprises a pair of upper magnet components, a pair of central magnet components and a pair of lower magnet components, in which each of the pair of magnet components are disposed on either side of the individual.

In some cases, only the pairs of upper and lower magnet components are moveably adjustable. In these cases, the method further comprises moving the location of the upper and lower pair of magnet components relative to the individual to obtain MR images of different imaging volumes of the individual. It should be noted that the movably adjustable magnet components in each pair as well as across different pairs can be configured to move in a symmetric fashion with respect to one another (i.e. move by the same amount at the same time) or in an asymmetric fashion with respect to one another (e.g. move by different amounts at the same or different times). Movement in an asymmetric fashion allows for imaging volumes to be generated such that they are located asymmetrically with respect to the movably adjustable magnet components (e.g. in opposed pairs)

In some cases, the pairs of upper, central and lower magnet components are all moveably adjustable. In these cases, the method further comprises moving the location of the upper, central and lower pair of magnet components relative to the individual to obtain MR images of different imaging volumes of the individual.

Figure 8A:
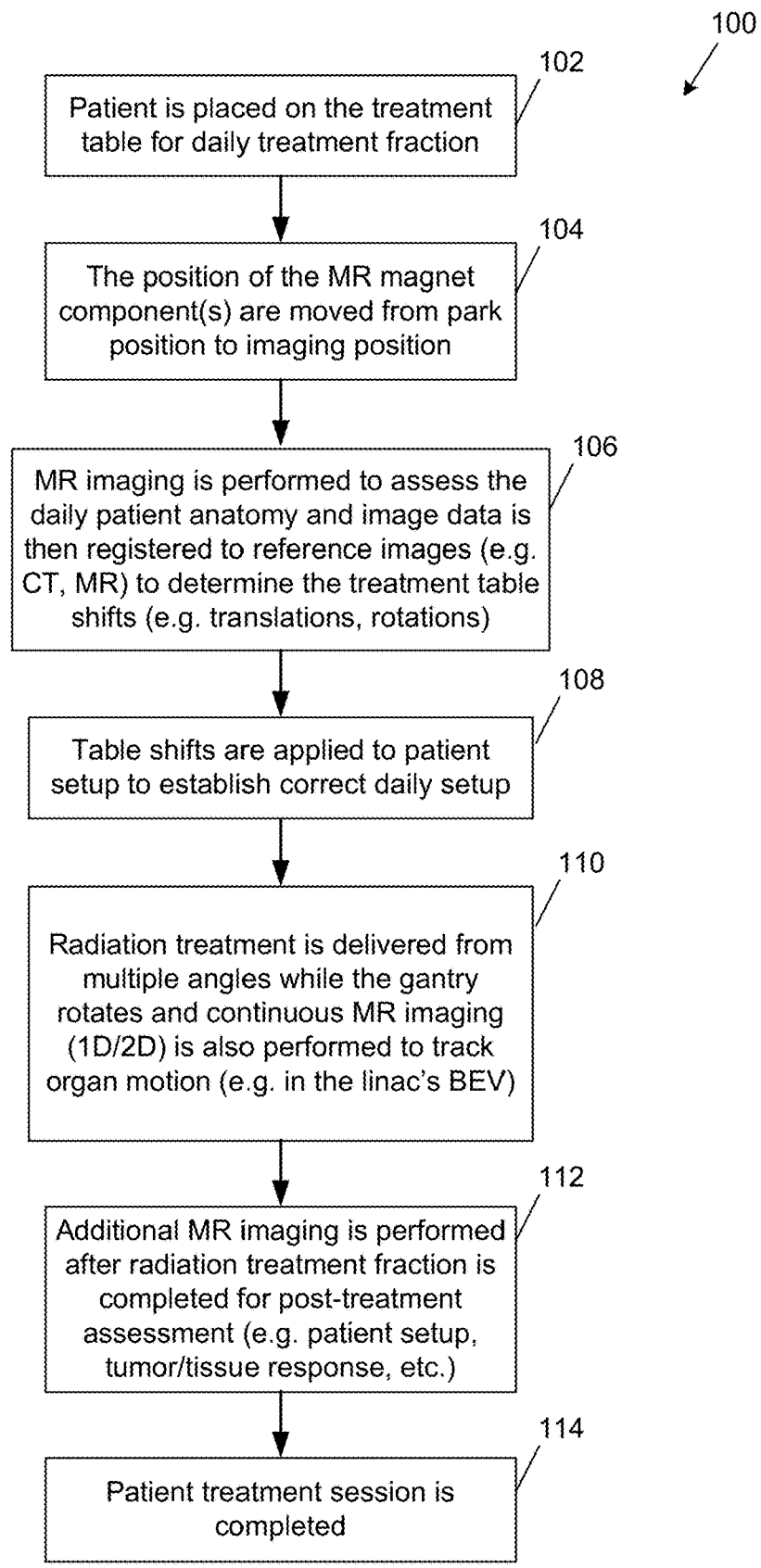
FIG. 8A shows an example embodiment of a method for operating an MR-linac system in accordance with the teachings herein.

Referring now to FIG. 8A, shown therein is an example embodiment of a method 100 for operating an MR-linac system in accordance with the teachings herein.

At 102, method 100 comprises placing a patient on the treatment table of a linac for a daily treatment fraction.

At 104, method 100 comprises moving the position of at least one MR magnet component of the MRI scanner moved from a park position to an imaging position.

At 106, method 100 comprises performing MR imaging to assess the daily patient anatomy and image data is then registered to reference images (e.g. CT, MR, etc.) to determine if treatment table shifts (e.g. translations, rotations) are needed.

At 108, method 100 comprises applying table shifts to the patient setup to establish the correct daily setup based on the determination made at 106.

At 110, method 100 comprises delivering radiation treatment from multiple angles while the gantry of the linac rotates during which MR imaging (e.g. 1D and/or 2D) may also be performed to track organ motion in the linac's BEV, for example. The MR imaging may be continuously performed during radiation treatment.

At 112, method 100 comprises performing additional MR imaging for post treatment assessment after the radiation treatment fraction is completed. The post-treatment assessment may include various types of information such as, but not limited to, patient setup, tumor/tissue response, and the like.

At 114, the patient treatment session is completed.

Figure 8B:
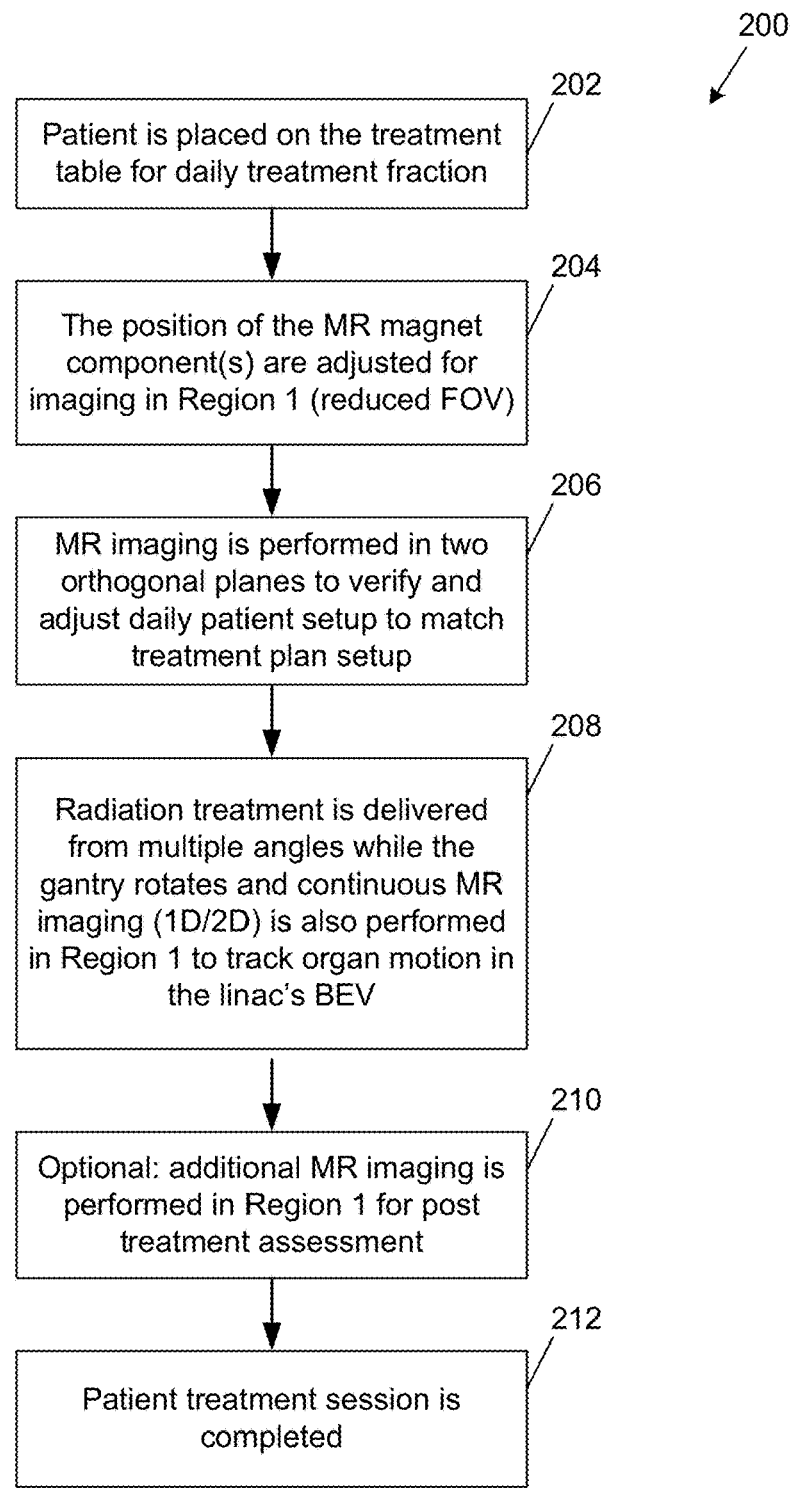
FIG. 8B shows an example embodiment of a method for operating an MR-linac system using a reduced FOV for MRI imaging.

Referring now to FIG. 8B, shown therein is an example embodiment of a method 200 for operating an MR-linac system using a reduced FOV for MRI imaging in accordance with the teachings herein. Acts 202, 208 and 212 of method 200 are similar to acts 102, 108 and 112 respectively of method 100 and therefore will not be discussed.

At 204, method 200 comprises positioning at least one of the moveably adjustable MR magnet components for imaging in Region 1 (e.g. a reduced FOV).

At 206, method 200 comprises performing MR imaging in two orthogonal planes to verify and adjust the daily patient setup to match the treatment plan setup.

At 210, method 200 comprises an optional act of performing additional MR imaging in Region 1 for post treatment assessment. The post-treatment assessment may include various types of information such as, but not limited to, patient setup, tumor/tissue response, and the like.

For MR-linac systems that are capable of performing MR and x-ray kV imaging, as per MR-linac systems 1, 3 and 4 described previously, the patient setup verification and real-time tracking of organ motion during treatment delivery may be achieved by utilizing either MR-only data or MR-kV composite data. This is described in more detail with regards to the workflow shown in FIG. 8C. The MR data can be acquired in a fixed plane relative to the linac beam (e.g. BEV of the linac), which rotates in unison with the system gantry. Thus, full volumetric data can be acquired during the rotation of the MR-linac system. The acquisition may be i) a snapshot per angle of rotation resulting in a 3D anatomical volume, or ii) a 2D-cine, which rapidly samples (e.g. 4 Hz) the anatomical volume (e.g. organ motion) in a single plane at each angle of gantry rotation. In other words, at each gantry angle multiple images may be acquired to track the organ motion. Extending this concept for multiple gantry angles, full volumetric data may be acquired which may be processed to generate 4D data sets in which 4D refers to volume (3D) and time dimension (1D). X-ray kV (cine or CBCT) is a common feature of a typical linac. However, in the corresponding MR-linac systems described herein, the x-ray kV may be combined via image registration with corresponding MR data (1D, 2D, 3D, or 4D) to generate composite representations of the daily patient anatomy. This may then be used to drive the treatment delivery.

Figure 8C:
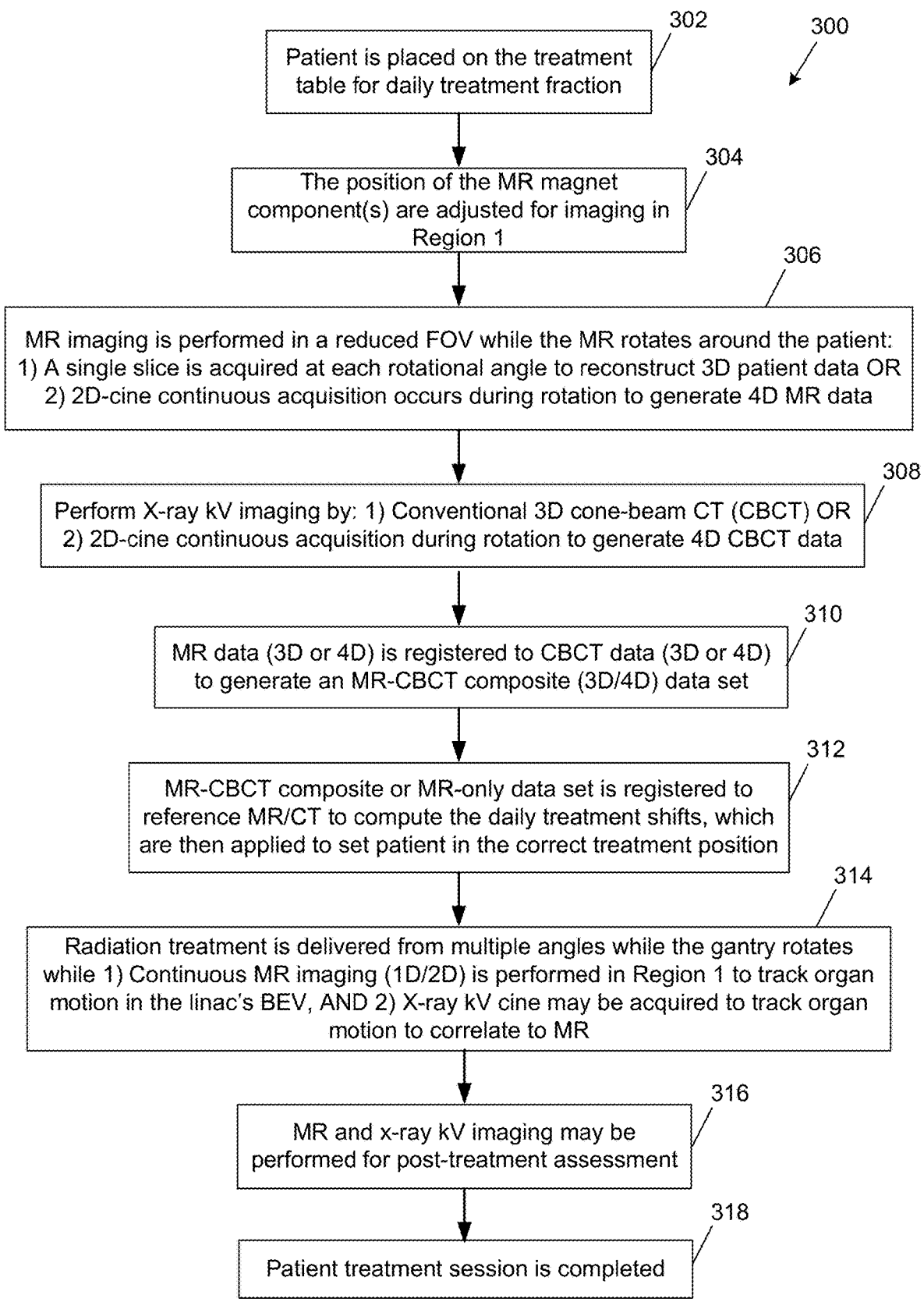
FIG. 8C shows an example embodiment of a method for operating an MR-linac system using MRI imaging and potentially another imaging modality such as X-ray KV.

Referring now to FIG. 8C, shown therein is an example embodiment of a method 300 for operating an MR-linac system using MRI imaging and potentially another imaging modality such as X-ray KV, for example, in accordance with the teachings herein. The MRI imaging may be done with a reduced FOV. For example, for the MR-linac embodiments that use both MR imaging and x-ray kV, the linac operation may be tailored to utilize both imaging modalities for patient setup verification and real-time tracking of organ/tumor target motion during radiation treatment delivery. Acts 302, 304, and 318 of method 300 are similar to acts 202, 204 and 212 respectively of method 200 and therefore will not be discussed.

At 306, method 300 comprises performing MR imaging in a reduced FOV while the magnet components of the MRI scanner rotates around the patient. A single slice may be acquired at each rotational angle to reconstruct 3D patient data OR 2D-cine continuous acquisition may occur during rotation to generate 4D MR data.

At 308, method 300 comprises performing X-ray kV imaging by 1) Conventional 3D cone-beam CT (CBCT) OR 2) 2D-cine continuous acquisition during rotation of the magnet components of the MRI scanner around the patient to generate 4D CBCT data.

At 310, method 300 comprises registering MR data (3D or 4D) to CBCT data (3D or 4D) to generate an MR-CBCT composite (3D/4D) data set.

At 312, method 300 comprises registering MR-CBCT composite or MR-only data to reference MR/CT data to compute the daily treatment shifts, which are then applied to set the patient in the correct treatment position.

At 314, method 300 comprises delivering radiation treatment from multiple angles while the gantry rotates. During radiation treatment continuous MR imaging (1D/2D) may be performed in Region 1 to track organ motion in the linac's BEV. In some cases, X-ray kV cine data may also be acquired during radiation treatment to track organ motion to correlate to the MR imaging data.

At 316, method 300 comprises performing MR and x-ray kV imaging for post-treatment assessment. Act 316 may be optional in certain cases and not performed.

Figure 8D:
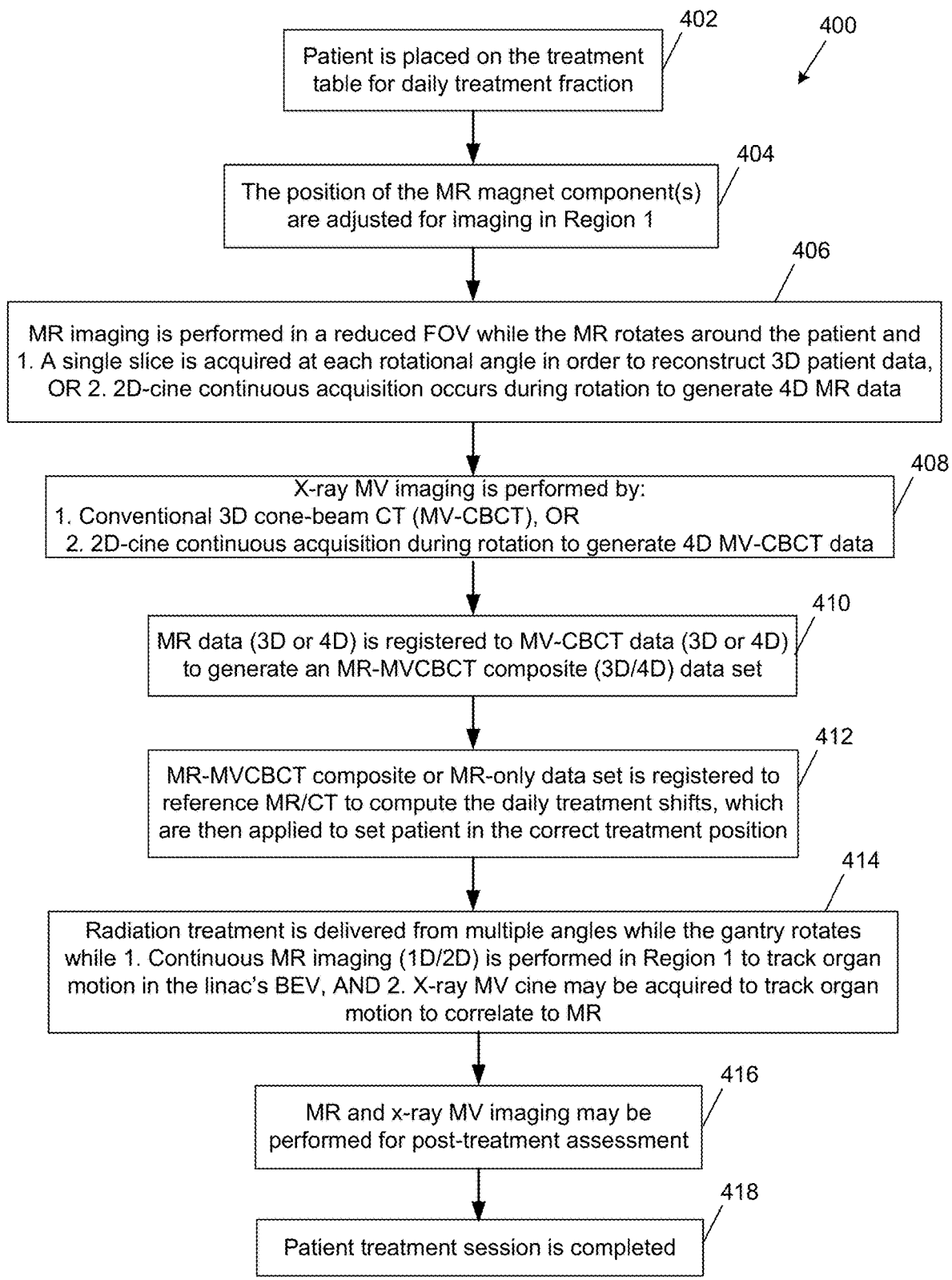
FIG. 8D shows another example embodiment of a method for operating an MR-linac system using MRI imaging and potentially another imaging modality such as X-ray MV.

Referring now to FIG. 8D, shown therein is an example embodiment of a method 400 for operating an MR-linac system using MRI imaging and potentially another imaging modality such as X-ray MV in accordance with the teachings herein. For example, for the MR-linac embodiments exhibiting both MR imaging and x-ray MV, the operation of the linac may be adapted to utilize both imaging modalities for patient setup verification and real-time tracking of organ/tumor target motion during treatment delivery. Acts 402, 404, 406 and 418 of method 400 are similar to acts 302, 304, 306 and 318 respectively of method 300 and therefore will not be discussed.

At 408, method 400 comprises performing X-ray MV imaging by using Conventional 3D cone-beam CT (MV-CBCT) or using 2D-cine continuous acquisition during rotation to generate 4D MV-CBCT data.

At 410, method 400 comprises registering MR data (3D or 4D) to MV-CBCT data (3D or 4D) to generate an MR-MVCBCT composite (3D/4D) data set.

At 412, method 400 comprises registering an MR-MVCBCT composite or an MR-only data set to reference MR/CT to compute the daily treatment shifts, which are then applied to set patient in the correct treatment position.

At 414, method 400 comprises delivering radiation treatment from multiple angles while the gantry rotates while continuous MR imaging (1D/2D) is performed in Region 1 to track organ motion in the linac's BEV and X-ray MV cine data may be acquired to track organ motion to correlate to the MR acquired data.

At 416, method 400 comprises performing MR and x-ray MV imaging for post-treatment assessment. Act 416 is optional.

Figure 8E:
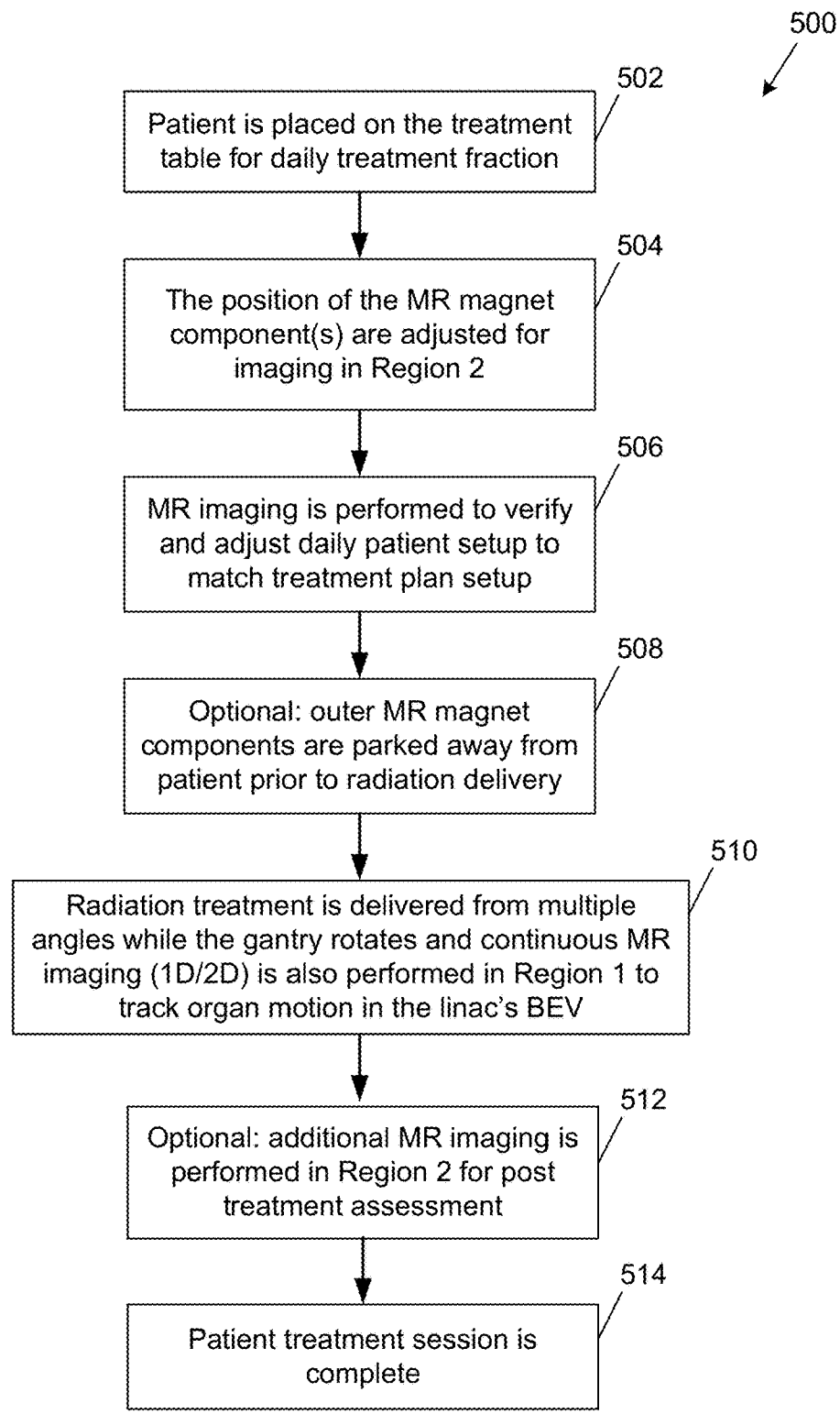
FIG. 8E shows another example embodiment of a method for operating an MR-linac system for combined imaging in two regions that may be used for different purposes.

Referring now to FIG. 8E, shown therein is an example embodiment of a method 500 for operating an MR-linac system for combined imaging in Region 1 and Region 2. Region 1 may be used for organ motion tracking during radiation delivery and Region 2 may be used for the verification of the patient's pre-treatment setup. Acts 502 and 514 of method 500 are similar to acts 102 and 114 respectively of method 100 and therefore will not be discussed.

At 504, method 500 comprises adjusting the position of the MR magnet components that are adjustable for imaging in Region 2.

At 506, method 500 comprises performing MR imaging to verify and adjust daily patient setup to match treatment plan setup.

At 508, method 500 comprises moving the outer (e.g. upper and lower) MR magnet components away from (e.g. parked away from) the patient prior to radiation delivery. Act 508 is optional.

At 510, method 500 comprises delivering radiation treatment from multiple angles while the gantry rotates. During this treatment, continuous MR imaging (1D and/or 2D) may be performed in Region 1 to track organ motion in the linac's BEV.

Figure 10:
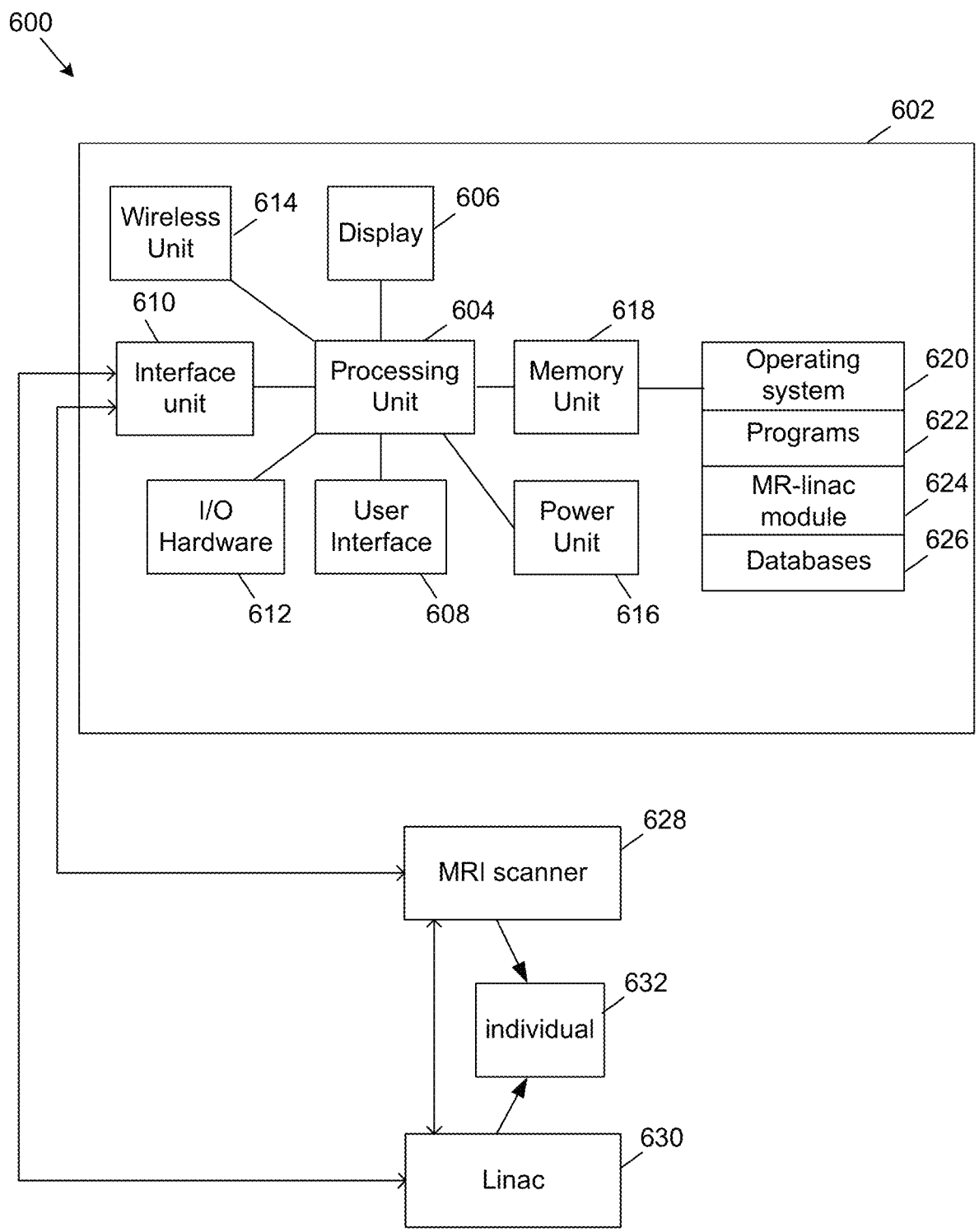
FIG. 10 shows a block diagram for an example embodiment of an MR-linac system in accordance with the teachings herein.

Referring now to FIG. 10, shown therein is a block diagram of an example embodiment of an MR-linac system 600 in accordance with the various teachings described herein. The MR-linac system 600 includes an operator unit 602, an MRI scanner 628 and a linac 630. The MRI scanner 628 has magnetic components that are moveable relative to the treatment beam of the linac 630 and/or the area of the individual that is to be imaged. Various embodiments have been described herein for the MRI scanner 628 and the linac 630 and how these components interact with one another to carry out one or more workflows.

The MR-linac system 600 is provided as an example and there can be other embodiments of the MR-linac system 600 with different components or a different configuration of the components described herein. The MR-linac system 600 further includes several power supplies (not all shown) connected to various components of the MR-linac system 600 as is commonly known to those skilled in the art. A user or operator, which may be a medical professional, interacts with the operator unit 602 to operate the MRI scanner 628 in conjunction with the linac 630 according to any of the various methods described herein. In some cases, there may be other operations that may be performed as is known by those skilled in the art.

The operator unit 602 comprises a processing unit 604, a display 606, a user interface 608, an interface unit 610, Input/Output (I/O) hardware 612, a wireless unit 614, a power unit 616 and a memory unit 618. The memory unit 618 comprises software code for implementing an operating system 620, various programs 622, an MR-linac module 624 and one or more databases 626. Many components of the operator unit 602 can be implemented using a desktop computer, a laptop, a tablet, a mobile device and the like.

The processing unit 604 controls the operation of the operator unit 602 and can be any suitable processor, controller or digital signal processor that can provide sufficient processing power processor depending on the configuration, purposes and requirements of the MR-linac system 600 as is known by those skilled in the art. For example, the processing unit 604 may be a high performance general processor. In alternative embodiments, the processing unit 604 can include more than one processor with each processor being configured to perform different dedicated tasks. In alternative embodiments, specialized hardware can be used to provide some of the functions provided by the processing unit 604.

The display 606 can be any suitable display that provides visual information depending on the configuration of the operator unit 602. For instance, the display 606 can be a cathode ray tube, a flat-screen monitor and the like if the operator unit 602 is a desktop computer. In other cases, the display 606 can be a display suitable for a laptop, tablet or handheld device such as an LCD-based display and the like.

The user interface 608 can include at least one of a mouse, a keyboard, a touch screen, a thumbwheel, a track-pad, a track-ball, a card-reader, voice recognition software and the like again depending on the particular implementation of the operator unit 602. In some cases, some of these components can be integrated with one another.

The interface unit 610 can be any interface that allows the operator unit 602 to communicate with other devices or computers. In some cases, the interface unit 610 can include at least one of a serial port, a parallel port or a USB port that provides USB connectivity. The interface unit 610 can also include at least one of an Internet, Local Area Network (LAN), Ethernet, Firewire, modem or digital subscriber line connection. Various combinations of these elements can be incorporated within the interface unit 610.

The I/O hardware 612 is optional and can include, but is not limited to, at least one of a microphone, a speaker and a printer, for example.

The wireless unit 614 is optional and can be a radio that communicates utilizing CDMA, GSM, GPRS or Bluetooth protocol according to standards such as IEEE 802.11a, 802.11b, 802.11g, or 802.11n. The wireless unit 614 can be used by the operator unit 602 to communicate with other devices or computers.

The power unit 616 can be any suitable power source that provides power to the operator unit 602 such as a power adaptor or a rechargeable battery pack depending on the implementation of the operator unit 602 as is known by those skilled in the art.

The memory unit 618 can include RAM, ROM, one or more hard drives, one or more flash drives or some other suitable data storage elements such as disk drives, etc. The memory unit 618 is used to store an operating system 620 and programs 624 as is commonly known by those skilled in the art. For instance, the operating system 620 provides various basic operational processes for the operator unit 602. The programs 622 include various user programs so that a user can interact with the operator unit 602 to perform various functions such as, but not limited to, viewing and manipulating data as well as sending messages as the case may be.

The MR-linac module 624 is used to operate the MRI scanner 628 in unison with the linac according to any of the various methods or workflows described herein. The MR-linac module 628 can be implemented as a single software module or as a collection of software modules that are directed to the various functions that are performed during the operation of the MR-linac system 600.

For example, the MR-linac module 628 comprises a plurality of sub-routines, classes, objects or functions for operating the MRI scanner 628 and moving at least one of the moveably adjustable magnet components of the MRI scanner 628 according to a particular MR imaging modality for a given imaging volume of the individual 632 who is being scanned and/or treated. For example, at least one of the moveably adjustable magnet components of the MRI scanner 628 may be moved from a park position to an imaging position to image a Region 1 or a Region 2 as described herein. Alternatively, the MR-linac module 628 may control at least one of the moveably adjustable magnet components to move to a park position away from the treatment beam of the linac 630 to avoid irradiation by or reduce exposure to the treatment beam.

The MR-linac module 624 further comprises a plurality of sub-routines, classes, objects or functions for operating the linac 630 in accordance with any of the methods or workflows described herein for providing desired radiation treatment to the individual 632.

The MR-linac module 624 may also comprise one or more sub-routines or classes for testing and/or calibrating the MRI scanner 628 and the linac 630 as is known by those skilled in the art.

The databases 626 can be used to store data for the MR-linac system 600 such as system settings, parameter values, and calibration data. The databases 626 can also store other information required for the operation of the programs 622 or the operating system 620 such as dynamically linked libraries and the like. The databases 626 can also be used to store at least one of image data and treatment data that is recorded while providing radiation treatment to the individual 632 or image data obtained when the individual 632 is only imaged.

The operator unit 602 comprises at least one interface that the processing unit 604 communicates with in order to receive or send information. This interface can be the user interface 608, the interface unit 610 or the wireless unit 614. For instance, information for calibrating the MR-linac system 600 for image correction or shimming can be inputted by someone through the user interface 608 or it can be received through the interface unit 610 from another computing device. The processing unit 604 can communicate with either one of these interfaces as well as the display 606 or the I/O hardware 612 in order to output information related to at least one of calibration, testing, MR imaging, other types of imaging, radiation treatment and post-assessment information in accordance with the various embodiments described herein. In addition, users of the operator unit 602 can communicate information across a network connection to a remote system for storage and/or further analysis. This communication can also include, but is not limited to, email communication, for example.

A user, such as a medical professional, can use the operator unit 602 to perform at least one of calibration, testing, MR imaging, other types of imaging, radiation treatment, and record post-assessment information in accordance with the various embodiments described herein. The user can also use the operator unit 602 to input information needed for system parameters that are needed for proper operation of the MRI scanner 628 and the linac 630 such as calibration information and system operating parameters including scan type, scan length, magnetic field strength, the type of sampling that is used, patient treatment protocols and various other parameters and information that are known to those skilled in the art. Data that is obtained during treatment, as well as parameters used for operation of the MR-linac system 600, may be stored in the memory unit 618. The stored data may include raw sampled data as well as processed image data such as MRI image data.

It should be noted that using an MRI scanner which has moveable magnet components relative to a linac or a volume of an individual receiving treatment from the linac results in greater flexibility for MR imaging and the generation of unique and arbitrary magnetic fields that may be homogeneous or inhomogeneous. For example, the magnet components shown in FIGS. 7A-7C can be moved to image various regions. For example, the central magnet components can be moved toward or away from an imaging volume of the individual being imaged such that a Region 1 may be imaged as previously described. Alternatively, the upper, central and lower magnet components may be moved relative to an imaging volume of the individual being imaged such that a Region 2 may be imaged as previously described. Also, various magnet component configurations may be used to have different orientations for the imaging volume as well as to orient the imaging volume in different ways relative to the treatment beam from the linac as was discussed with regards to FIGS. 2A to 6B.

It should also be noted that a monopole configuration may be used for the magnet components of the MRI scanner in which magnet components are only position on one side of the individual being imaged and possibly treated. This allows for slice imaging of a Region 1 with an ellipsoid shape as described previously. The monopole magnet components can be moved closer to or further away from the individual being imaged to image different portions of the individual.

It should be noted that the MR-linac system 600 may be modified so that the operator unit 602 is only coupled with the MRI scanner 628 and there is no linac. In this case the system is an MRI system which has at least one movably adjustable magnet component to provide increased flexibility for obtaining MR images of an individual. The MRI scanner functions as described in the various embodiments of the MR-linac systems and workflows/methods described herein except there is no radiation treatment elements. It should be understood that the MRI scanner can still be mounted on robotic arms or other elements that are moveable so that at least one of the magnet components can be moved to different positions with respect to a desired imaging volume for the individual 632.

Figure 11:
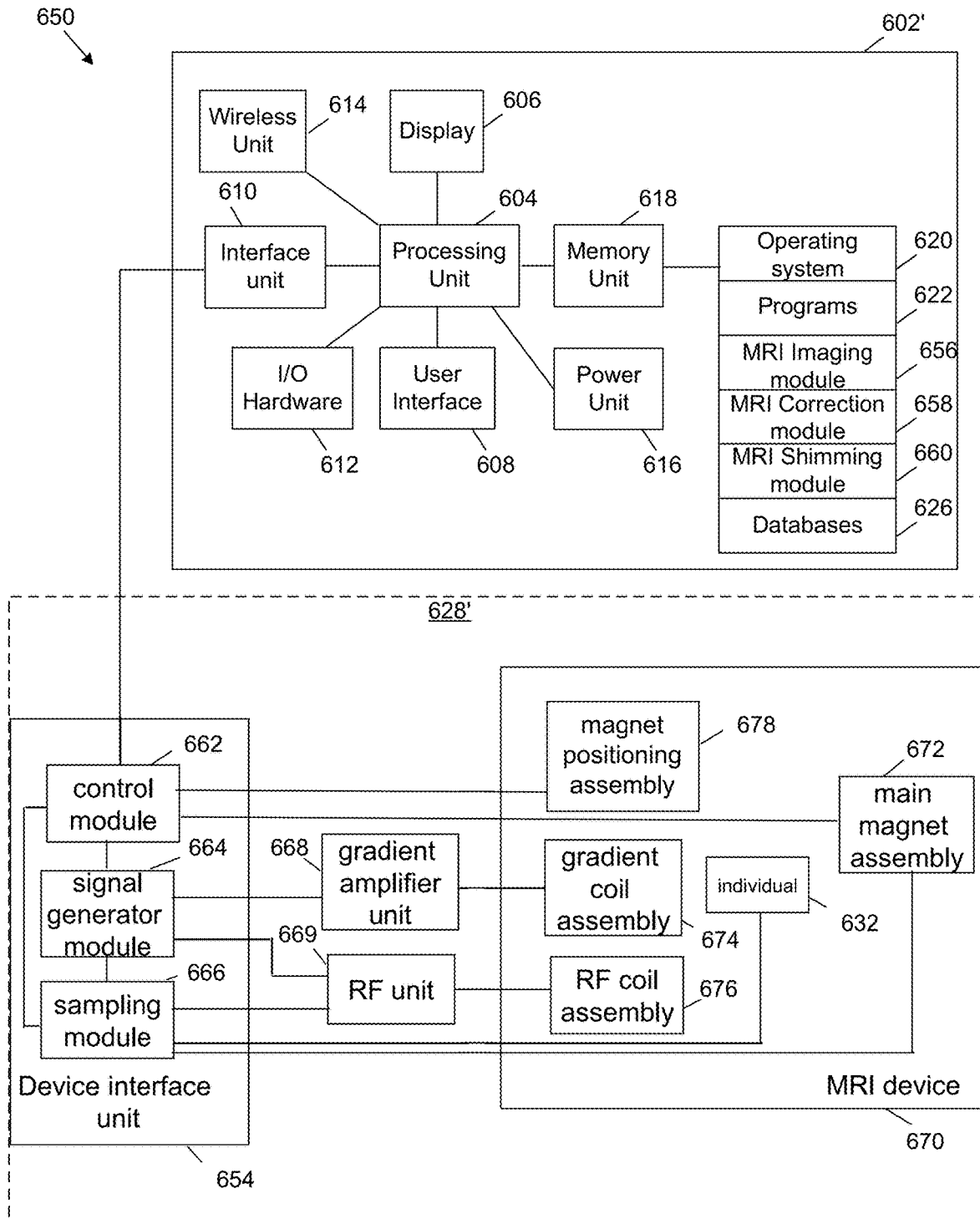
FIG. 11 shows a block diagram for an example embodiment of an MRI system with at least one movably adjustable magnet component in accordance with the teachings herein.

Referring now to FIG. 11, shown therein is a block diagram for an example embodiment of an MRI system 650 with at least one movably adjustable magnet component in accordance with the teachings herein. The MRI system 650 includes an operator unit 602' which is similar to the operator unit 602 but has been modified to only provide MRI imaging and related functions in accordance with one of the various embodiments described herein related to using movably adjustable magnet components for increased MRI imaging flexibility. Accordingly, the MR-linac module 624 is replaced with the MRI imaging module 656, the MRI correction module 658 and the MRI shimming module 660 Furthermore, an example embodiment of an MRI scanner 628' is shown although there can be other embodiments with different components or a different configuration of the components described herein as is known to those skilled in the art as long as the magnet positioning assembly 678 is implemented to allow the magnet components to be moved to various positions relative to a desired imaging volume of the individual 632 according to at least one of the MR-linac system and method/workflow embodiments described herein.

The MRI imaging module 656 may be used to control the MRI scanner 628' to obtain MR images of a subject, a phantom or some other object as is known by those skilled in the art. The MRI imaging module 656 may also be used to move at least one of the magnet components of the MRI scanner 628; to various positions with respect to a desired imaging volume of the individual in accordance with at least one of the MR-linac system and associated method embodiments described herein.

The MRI correction module 658 may be used to measure, characterize, and correct system-related geometric distortions. In at least some embodiments, the MRI correction module 36 may also be configured to perform Quality Assurance (i.e. QA) monitoring of the MR image quality. Various techniques may be used for geometric distortion correction and quality assurance as is known by those skilled in the art.

The MRI shimming module 660 may be used to correct for inhomogeneities of the magnetic field ($B_0$) produced by the main magnet. This correction is performed according to at least one of the various embodiments described herein.

The MRI imaging module 656, the MRI correction module 658 and the MRI shimming module 660 are typically implemented using software, but may be implemented using FPGA or application specific circuitry in some cases.

The MRI scanner 628' includes an MRI device 670 with components for generating magnetic fields to magnetize and scan the individual 632 using various magnet component positions for increased imaging flexibility. The MRI device 670 includes a main magnet assembly 672, a gradient coil assembly 674, an RF coil assembly 676 and the magnet positioning assembly 678 that can move at least one magnet component of the MRI device 670 relative to the individual 632. The magnet positioning assembly 672 may comprise one, two or more robotic arms or other mechanical elements that can be used to move the position of at least one magnet component.

The main magnet assembly 672 may be a resistive magnet or a superconductive magnet which both require a power supply (not shown) for operation. Alternatively, the main magnet assembly 672 may include a permanent magnet.

A shim power supply (not shown) may also be used to energize shim coils (not shown) that are used with the main magnet assembly 672 to correct any non-uniformity in the main magnetic field that is generated by the main magnet assembly 672.

In some embodiments, there may also be elements that provide mechanical shimming either alone or in combination with the aforementioned electrical shimming. For example, the mechanical shimming may comprise a collection of segments of ferromagnetic material that can be placed in the vicinity of the magnet elements. The ferromagnetic material may have various shapes, sizes, and material/magnetic properties in order to correct for non-uniformity in the magnetic field generated by the main magnet assembly 672.

Typically, the gradient coil assembly 674 and the RF coil assembly 676 are co-located with the magnet positioning assembly 678 in accordance with the various embodiments described herein for the MR-linac systems.

The gradient coil assembly 674 is energized to generate magnetic field gradients Gx, Gy and Gz that are superimposed on the main magnetic field $B_0$ that is produced by the main magnet assembly 672.

The RF coil assembly 674 may include one set of coils for transmitting and receiving RF energy or separate transmit and receive coils for separately transmitting and receiving RF energy, respectively. The RF coil assembly 676 generates the RF excitation pulses which, in combination with the magnetic field gradients Gx, Gy and Gz, encode spatial information into the NMR signals generated by the region of the individual 632 being imaged. The NMR signals are also sensed by the RF coil assembly 676.

The MRI scanner 628' further comprises a device interface unit 654 that includes a control module 662, a signal generator module 664, and a sampling module 666. The MRI scanner 628' further includes a gradient amplifier unit 668 and an RF unit 669. The device interface unit 654, the gradient amplifier unit 668 and the RF unit 669 may be referred to as interface circuitry that interfaces the operator unit 602 to the MRI scanner 628'.

The control module 662 receives instructions from the operator unit 602' to follow a particular MRI scan protocol for imaging the individual 632. The control module 662 instructs the magnet positioning assembly 678 to move at least one of the movably adjustable magnet components into the proper position according to the MRI scan protocol and the desired imaging volume. Depending on the type of magnet that is used in the main magnet assembly 672, the control module 662 may also provide certain control signals to the main magnet assembly 672 to control various parameters of the main magnetic field $B_0$ that is generated by the main magnet assembly 672. The control module 662 also instructs the signal generator module 664 to generate a particular gradient waveform sequence and pulse sequence that will be applied to the gradient coil assembly 674 and the RF coil assembly 676 by the gradient amplifier unit 668 and the RF unit 669, respectively. The control module 662 can also provide timing information to the sampling module 666, including the length and type of data acquisition that is used for sampling data from the RF coil assembly 676 during use.

The signal generator module 664 produces the proper gradient waveforms Gx, Gy and Gz as well as RF waveforms needed for a variety of MRI scan protocols including spin echo, fast spin echo, and the like. The signal generator module 664 receives control signals from the control module 662 to set the shape and timing of the magnetic field gradients that are generated by the gradient coil assembly 674. Based on these control signals, the signal generator module 664 also generates RF waveforms for setting the amplitude, shape and timing of the RF pulses that are produced by the RF coil assembly 676. Both of the sets of gradient and RF waveforms may be created digitally and the signal generator module 664 may further include a digital to analog converter (DAC) (not shown) that converts the digital waveforms to corresponding analog waveforms. The signal generator module 664 may further include a switching device that connects the output of the DAC to either the gradient amplifier unit 668 or the RF unit 669. Alternatively, separate DACs may be used to send the gradient pulse waveforms and the RF waveforms to the gradient amplifier unit 668 and the RF unit 669, respectively. The signal generator module 664 may also generate timing signals that are sent to the sampling module 664 so that the NMR signals are correctly sampled depending on the type of gradient and RF waveforms that are sent to the gradient coil assembly 674 and the RF coil assembly 676 respectively.

The gradient amplifier unit 668 typically includes three amplifiers (not shown), i.e. one amplifier for each of the gradient pulse waveforms Gx, Gy and Gz. The gradient amplifier unit 668 receives the analog version of the gradient pulse waveforms, amplifies these waveforms and applies them to the corresponding coils in the gradient coil assembly 674. In alternative embodiments, the gradient amplifier unit 668 may receive digital waveforms and can include a DAC for processing and applying these waveforms to the corresponding coils.

The RF unit 669 generally includes a transceiver, a transmit amplifier, a receive amplifier and an analog to digital converter (ADC) (all not shown) as is commonly known to those skilled in the art. The transceiver receives the RF waveforms from the signal generator module 664 and modulates these waveforms to generate RF excitation pulses. The transmit amplifier receives and amplifies the RF excitation pulses and provides the amplified RF excitation pulses to the RF coil assembly 676 which radiates these pulses to the individual 632. After excitation, the NMR signals generated by the individual 632 are sensed by the RF coil assembly 676. The receive amplifier then receives the sensed NMR signals from the RF coil assembly 676, amplifies the sensed NMR signals and provides the amplified NMR signals to the transceiver. The transceiver then pre-processes the amplified NMR signals by applying demodulation and filtering. The pre-processed NMR signals are then sent to the sampling module 666 for sampling.

The sampling module 666 receives and samples the pre-processed NMR signals to produce raw k-space data. The k-space data provides information about the MRI scan in the spatial frequency domain. In some cases, the sampled k-space data may contain spatial data for each imaging "slice" that is measured and thus can be arranged into a series of two-dimensional (2D) arrays. One may interpret the k-space data in both the x and y directions as the phase information of the nuclear magnetic spins, or one may interpret the k-space data in both the x and y directions as the spatial frequency information of the MR images. In addition, k-space data along the negative x-axis and/or the negative y-axis are also typically acquired, and the accumulated phase of the nuclear magnetic spins increases as one moves away from the origin of the k-space domain. The center of the 2D k-space data array represents DC and the edges of the 2D k-space data array correspond to high spatial frequencies. Alternatively, in some cases the MR images are not necessarily acquired in a slice-by-slice fashion, and various other techniques can be used as is known by those skilled in the art.

The raw k-space data is sent to the control module 662 where it may be further processed and/or sent to the processing unit 604 for processing and storing in the memory unit 618. In both cases, processing produces MRI image data from the raw k-space data. The MRI image data may be displayed on the display 606. The MRI image data may also be further image processed by either the control module 662 or the processing unit 602'. Processing typically includes application of the inverse 2D Fourier Transform to generate image data from a 2D k-space data set. Accordingly, the control module 662 may further include dedicated processing circuitry such as an array processor, as is well known to those skilled in the art, that inverse Fourier transforms the raw k-space data. The array processor is used to speed up numeric computation. Other types of algorithms may be applied to the MRI image to improve the quality of the MRI images, as are described herein.

Alternatively, in some embodiments, the sampling module 666 may also be connected to the main magnet assembly 672 to record data about the main magnetizing/polarizing magnetic field.

In an alternative embodiment, the moveably adjustable MRI scanner components (by a robotic elements for example) and the linac head may be mechanically mounted on a common circular gantry, which replaces the L-shaped structure depicted in FIGS. 7A-7C. The MR magnet component may travel from the periphery of the gantry towards its inner volume to generate imaging Regions 1 and 2. This configuration allows for a bore-like opening inside the gantry opening, which is may be used for patient and treatment table access for both imaging and treatment delivery purposes. This alternative embodiment preserves the main functionality of the system regarding the separate and in-unison operation of the MRI scanner and the linac.

For at least one of the example embodiments described herein, the MR magnet components may comprise permanent magnets.

For at least one of the example embodiments described herein, the MR magnet components may comprise copper wire wound and water-cooled coils (or winding segments).

For at least one of the example embodiments described herein, the MR magnet components may comprise superconducting magnetic coil assemblies that are cooled with liquid He or Nitrogen.

For at least one of the example embodiments described herein, the MR magnet components may comprise a hybrid combination of the following elements: permanent magnets, copper wire wound and water-cooled coil (or winding segments) and superconducting magnetic coil assemblies that are cooled with liquid He or Nitrogen.

For at least one of the example embodiments described herein, the magnetic field ($B_0$) may also be designed to be adjustable as a function of one, several of or all of the following parameters: i) the imaging task, such as static or dynamic/real-time imaging, ii) the FOV dimension (e.g. small, medium or large), iii) the anatomical site (since different anatomical sites require different levels of RF signal sensitivity), iv) the type of acquisition (e.g. single-slice or multi-slice), or v) the image quality.

For at least one of the example embodiments described herein, the magnetic field ($B_0$) configuration may also be configured to take into account the relative distribution and orientation of all magnet components with regards to the linac radiation beam in order achieve at least one of: a) minimizing the exposure of coils (e.g. RF transmit/receive coils, gradient coils, magnet coils) to damaging radiation, b) minimizing the fringe field at the linac waveguide to reduce efforts/costs for additional magnetic shielding (e.g. passive and/or active), and c) minimizing the skin dose effects by deflecting the stray electrons traveling toward the imaging volume.

For at least one of the example embodiments described herein which use multiple magnet components, it is possible to generate a magnetic field ($B_0$) with a certain spatially non-homogeneous distribution that minimizes the dosimetric effects due to the presence of the MR's magnetic field. For example, a uniform magnetic field ($B_0$) would tend to push the secondary electrons towards one direction whereas a spatially non-uniform magnetic field ($B_0$) would spread the electrons trajectories in multiple directions, avoiding their focusing effects and the generation of dose deposited hot/cold spots.

Imaging with a Non-Homogeneous Main Magnetic Field

Figure 9A:
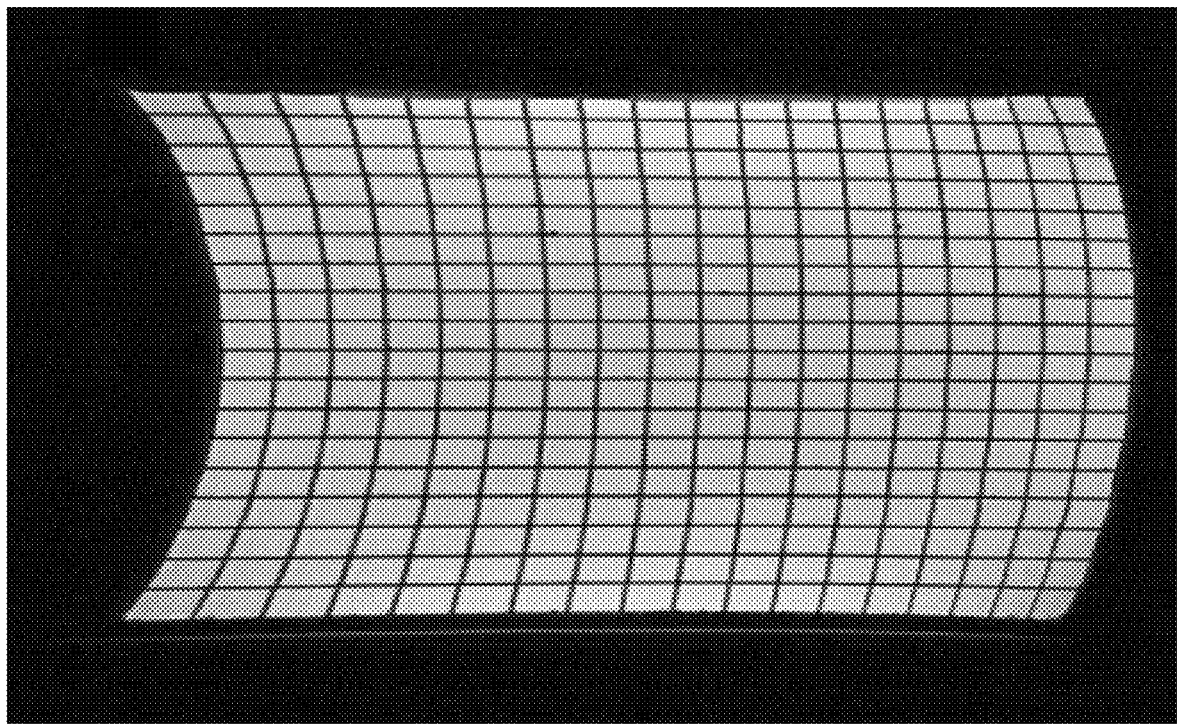
FIG. 9A shows an example of an image of with geometric distortion due to a reduction in magnetic field homogeneity.

Local field inhomogeneities introduce additional dephasing of the spins, which translates into an incorrect representation of the spatial location where the signal resides. A conventional image reconstruction algorithm can be used that performs Fourier transformations assuming an ideally homogeneous magnetic field ($B_0$). As a consequence, any perturbation of the signal will result in geometric distortions in the reconstructed images. For example, FIG. 9A shows an example of an image with the type of geometric distortion that can occur due to a reduction in magnetic field homogeneity. In particular, image spatial integrity is affected by the level of homogeneity of the magnetic field ($B_0$). Signal loss occurs at the periphery of the imaging volume due to additional dephasing of the spins.

Figure 9B:
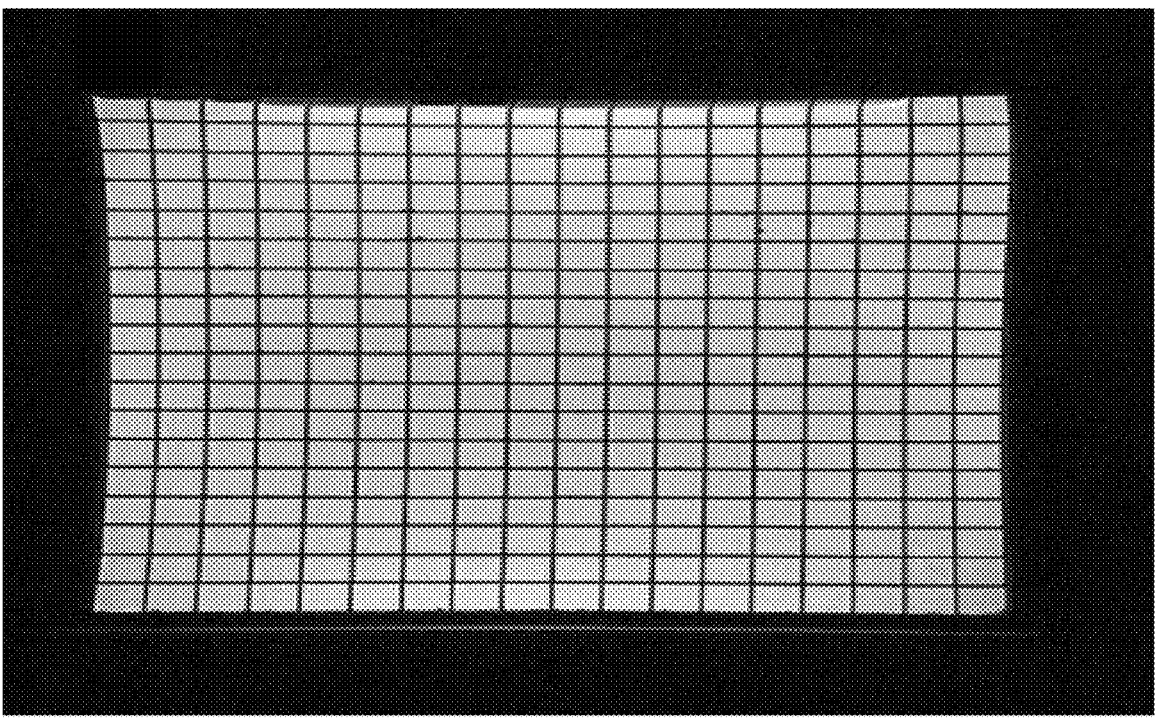
FIG. 9B shows an example of a distortion free image based on taking the magnetic field distribution into account.

To account for the field inhomogeneities, the magnetic field ($B_0$) may be mapped by using experimental measurements (e.g., Hall probe, phantom), for example. By using the prior knowledge of the distribution of the local magnetic field ($B_0$), Fourier transformations can be performed along the iso-field lines (i.e. curved trajectories/planes featuring the same field strength) and subsequently images can be reconstructed that are relatively free of spatial distortions. For example, FIG. 9B shows an example of a distortion-free image based on taking the magnetic field distribution into account.

In alternative embodiments, the image data can also be reformatted and presented to the user in any arbitrary plane.

Hardware components required for the imaging with a non-homogeneous main magnetic field are discussed in the literature[33-36] which are hereby incorporated by reference in their entirety.

The various embodiments of the MR-linac systems described herein may be constructed such that they provide at least one of the following several advantages:

A. Low manufacturing cost: the cost is expected to be a fraction of the cost of a conventional MR system due to a simpler design. In addition, since there are less strict constraints on the homogeneity of the magnetic field ($B_0$), this results in the use of cheaper materials, cheaper maintenance, and cheaper shimming requirements.

B. Compact design: the MR-linac systems described herein can be built as a standalone apparatus or it can be integrated as an add-on component for an existing RT platform such as: B1) adding robotic arms on a linac to replace the CBCT (X-ray based imaging) system for an external RT, B2) replace the MV panel of a typical linac (facing the treatment MV beam) with an MR monopole magnet, thus providing both kilovoltage (kV) and MR imaging, B3) integrating the MR monopole with the MV panel, thus providing three imaging modalities on a linac (i.e. x-ray kV, MV and MRI); B4) integration with an existing robotic linac system (e.g. CyberKnife™), or B5) integration with a brachytherapy interventional suite for needle tracking (e.g. seed implants, biopsies, etc.).

C. Adjustability: the magnet components generating the magnetic field ($B_0$) can be attached to robotic arms so that they can be moved closer to or further away from the imaging volume with a desired amount of patient proximity, which allows for improved patient access and comfort (e.g. reduction of claustrophobia).

D. Low fringe fields: the footprint of the smaller magnet components facilitates a simpler implementation for magnetic decoupling (active or passive) between the MR and the linac. For certain designs, magnetic decoupling may not be necessary (e.g. an MRI scanner featuring imaging for Region 1 only).

E. System fit in existing vaults: previously proposed MR-linac systems may require a rotational clearance around the patient of about 3-4 m, which leads to a significant and costly linac vault, and this re-design may not be needed with at least one of the various MR-linac embodiments described herein.

It should be noted that in the various embodiments described herein of MR systems and MR-linac systems there can be embodiments in which there is only one movably adjustable magnet component, such as the monopole MR magnet, similar to what was described in conjunction with FIG. 2A. There are also other embodiments of MR systems and MR-linac systems where there are additional magnets which may not be movably adjustable. Furthermore, there are also other embodiments of MR systems and MR-linac systems in which there are two or more movably adjustable magnet components such as the embodiment shown in FIGS. 7A-7C, for example.

Furthermore, it should be understood that the movably adjustable magnet components described herein are movable to different positions which are different distances away from the desired imaging volume of an object, and hence these moveably adjustable magnet components are not just moved to rotate around the desired imaging volume at the same distance, as is done conventionally.

At least some of the elements of the MR-linac system that are implemented via software may be written in a high-level procedural language such as object oriented programming or a scripting language. Accordingly, the program code may be written in C, C++, SQL or any other suitable programming language and may comprise modules or classes, as is known to those skilled in object oriented programming. It should also be understood that at least some of the elements of the various MR-linac systems or MRI systems described herein that are implemented via software may be written in assembly language, machine language or firmware as needed. In either case, the program code can be stored on a storage media or on a computer readable medium that is readable by a general or special purpose programmable computing device having a processor, an operating system and the associated hardware and software that is necessary to implement the functionality of at least one of the embodiments described herein. The program code, when read by the computing device, configures the computing device to operate in a new, specific and predefined manner in order to perform at least one of the methods described herein.

Furthermore, at least some of the software components described herein are capable of being distributed in a computer program product comprising a computer readable medium that bears computer usable instructions for one or more processors. The medium may be provided in various forms, some of which are non-transitory in nature. The medium may include, but is not limited to, various non-transitory elements such as one or more diskettes, compact disks, tapes, chips, USB keys, external hard drives, and magnetic and electronic storage media. In other cases, the medium may include, but is not limited to, various transitory media such as wire-line transmissions, satellite transmissions, Internet transmissions or downloads, digital and analog signals, and the like. The computer useable instructions may also be in various forms, including compiled and non-compiled code.

While the applicant's teachings described herein are in conjunction with various example embodiments provided for illustrative purposes, it is not intended that the applicant's teachings be limited to such embodiments. On the contrary, the applicant's teachings described and illustrated herein encompass various alternatives, modifications, and equivalents, without departing from the embodiments described herein.

REFERENCES

1. World Health Organization, International Agency For Research on Cancer, Press Release No. 223, Dec. 12, 2013.
2. B. Fallone, B. Murray, S. Rathee, T. Stanescu, S. Steciw, S. Vidakovic, E. Blosser and D. Tymofichuk, Medical physics 36 (6), 2084-2088 (2009).
3. B. W. Raaymakers, J. J. Lagendijk, J. Overweg, J. G. Kok, A. J. Raaijmakers, E. M. Kerkhof, R. W. van der Put, 1. Meijsing, S. P. Crijns, F. Benedosso, M. van Vulpen, C. H. de Graaff, J. Allen and K. J. Brown, Physics in medicine and biology 54 (12), N229-237 (2009).
4. The MRIdian System, A complete MRI-Guided Radiation Therapy System, viewable on the Internet at the ViewRay homepage, 2012.
5. J. Dempsey, B. Dionne, J. Fitzsimmons and e. al., Medical physics 33 (6), 2254 (2006).
6. D. Jaffray, M. Carlone, C. Menard and S. Breen, Proc. SPIE 7622, 762202 (2010).
7. T. Tadic, D. Jaffray and T. Stanescu, 5th NCIGT and NIH Image Guided Therapy Workshop, Boston, USA (2012).
8. S. P. Crijns, J. G. Kok, J. J. Lagendijk and B. W. Raaymakers, Physics in medicine and biology 56 (15), 4815-4825 (2011).
9. J. Yun, M. Mackenzie, S. Rathee, D. Robinson and B. G. Fallone, Medical physics 39 (7), 4423-4433 (2012).
10. J. St Aubin, S. Steciw and B. G. Fallone, Medical physics 37 (9), 4755-4761 (2010).
11. J. St Aubin, D. M. Santos, S. Steciw and B. G. Fallone, Medical physics 37 (9), 4916-4923 (2010).
12. B. Burke, M. Lamey, S. Rathee, B. Murray and B. G. Fallone, Physics in medicine and biology 54 (8), 2483-2492 (2009).
13. M. Lamey, B. Burke, E. Blosser, S. Rathee, N. De Zanche and B. G. Fallone, Physics in medicine and biology 55 (4), 995-1006 (2010).
14. C. Kirkby, T. Stanescu, S. Rathee, M. Carlone, B. Murray and B. G. Fallone, Medical physics 35 (3), 1019-1027 (2008).
15. C. Kirkby, B. Murray, S. Rathee and B. G. Fallone, Medical physics 37 (9), 4722-4732 (2010).
16. A. J. Raaijmakers, B. W. Raaymakers and J. J. Lagendijk, Physics in medicine and biology 50 (7), 1363-1376 (2005).
17. A. J. Raaijmakers, B. W. Raaymakers and J. J. Lagendijk, Physics in medicine and biology 52 (14), 4283-4291 (2007).
18. B. M. Oborn, P. E. Metcalfe, M. J. Butson, A. B. Rosenfeld and P. J. Keall, Medical physics 39 (2), 874 (2012).
19. A. Keyvanloo, B. Burke, B. Warkentin, T. Tadic, S. Rathee, C. Kirkby, D. M. Santos and B. G. Fallone, Medical physics 39 (10), 6509-6521 (2012).
20. B. Burke, B. G. Fallone and S. Rathee, Physics in medicine and biology 55 (3), 735-746 (2010).
21. B. Burke, A. Ghila, B. G. Fallone and S. Rathee, Medical physics 39 (8), 5004-5014 (2012).
22. S. J. Hoogcarspel, S. P. Crijns, J. J. Lagendijk, M. van Vulpen and B. W. Raaymakers, Physics in medicine and biology 58 (6), 1925-1932 (2013).
23. J. St Aubin, S. Steciw and B. G. Fallone, Physics in medicine and biology 55 (16), 4861-4869 (2010).
24. D. E. Constantin, R. Fahrig and P. J. Keall, Medical physics 38 (7), 4174-4185 (2011).
25. D. M. Santos, J. St Aubin, B. G. Fallone and S. Steciw, Medical physics 39 (2), 788-797 (2012).
26. A. J. Raaijmakers, B. W. Raaymakers and J. J. Lagendijk, Physics in medicine and biology 53 (4), 909-923 (2008).
27. B. W. Raaymakers, A. J. Raaijmakers, A. N. Kotte, D. Jette and J. J. Lagendijk, Physics in medicine and biology 49 (17), 4109-4118 (2004).
28. H. Xu, IEEE TRANSACTIONS ON MAGNETICS 36 (2), 476-483 (2000).
29. S. Russenschuck, Int J NUMERICAL MODELLING: ELECTRONIC NETWORKS, DEVICES AND FIELDS 9, 45-57 (1996).
30. S. Crozier and D. Doddrell, J Magn Reson 127 (2), 233-237 (1997).
31. S. Crozier, L. Forbes and D. Doddrell, Meas Sci Technol 9 (1), 113-119 (1998).
32. W. Smythe, *Static and Dynamic Electricity*. (McGraw-Hill, 1950).
33. D. Thayer, Brigham Young University, 2004.
34. V. Arpinar and B. Eyuboglu, IFMBE Proceedings 22, 410-413 (2008).
35. V. Arpinar and B. Eyuboglu, IFMBE Proceedingss 25, 432-435 (2009).
36. A. Yilmaz and B. Eyuboglu, IFMBE Proceedings 14 (3), 1480-1483 (2003).

The invention claimed is:

1. A Radio-Therapy (RT) system for radiation treatment and Magnetic Resonance (MR) imaging, wherein the system comprises:
   a gantry that is rotatable;
   a radiation source coupled to the gantry and comprising a radiation source head, the radiation source configured to generate a treatment beam for an object during use, the treatment beam having a treatment beam direction from the radiation source head to the object; and
   a Magnetic Resonance Imaging (MRI) scanner coupled to the radiation source or the gantry, the MRI scanner being configured to perform the MR imaging and including:
      at least two magnet components, each of the at least two magnet components comprising two or more coils that together form a coil ensemble that creates an imaging target volume that has an ellipsoidal shape with a first elliptical cross-section in a first plane and a second elliptical cross-section in a second plane orthogonal to the first plane, the first elliptical cross-section having a first major axis and a first minor axis and the second elliptical cross-section having a second major axis and a second minor axis, where the second minor axis is smaller than both the first major axis and the first minor axis;
      wherein the at least two magnet components are:
         movable around the object via rotation of the gantry to image at least one region of the object within the imaging target volume before, during, or after treatment with the treatment beam; and positionable relative to the treatment beam such that the first elliptical cross-section of the imaging target volume is orthogonal to the treatment beam direction and in a beam's eye view of the treatment beam.

2. The RT system of claim 1, wherein at least one of the at least two magnet components is movably adjustable and wherein the MRI scanner is further configured to operate in a first operation mode, where the at least one of the at least two magnet components is configured to move away from the object to perform imaging with the imaging target volume; and in a second operation mode, where the at least one of the at least two magnet components is configured to move closer to the object to perform imaging with a larger field of view than that in the first operation mode.

3. The RT system of claim 2, wherein the at least two magnet components are mounted such that a magnetic field in the imaging volume is oriented in-line with the treatment beam thereby preserving a capability for kV imaging, and the RT system further comprises kV imaging components that are mounted and oriented at 90° with respect to the treatment beam direction thereby allowing for dual MRI and X-ray kV imaging.

4. The RT system of claim 3, wherein the RT system is configured to perform the duel MRI and X-ray kV imaging during rotation of the linac and magnet components around the object.

5. The RT system of claim 3, wherein the RT system further comprises an x-ray megavoltage (MV) panel detector that is mounted to face the treatment beam during the dual MRI and X-ray MV imaging.

6. The RT system of claim 1, wherein the RT system further comprises a processor configured to perform single slice reconstruction on MR imaging data obtained for the object and the processor is further configured to perform image reconstruction based on assuming a non-uniform magnetic field is generated by the MRI scanner and based on prior knowledge of a spatial distribution of inhomogeneities of the magnetic field for a second region that includes and extends beyond the at least one region of the object.

7. The RT system of claim 1, wherein the radiation source is a linear accelerator (linac), and the MRI scanner and the linac are mechanically coupled to a common gantry.

8. The RT system of claim 7, wherein the RT system further comprises a processor configured to execute instructions to cause the MRI scanner to perform multi-slice MR imaging for the object by rotating the MRI scanner in unison with the gantry and obtaining multiple images at different gantry angles.

9. The RT system of claim 1, wherein the two or more coils of the coil ensemble have radii and spatial locations that are selected for optimizing at least one of coil power dissipation, total volume of the two or more coils, coil conductor mass, and a physical footprint of the coil ensemble required to generate the imaging target volume during use.

10. The RT system of claim 4, wherein the total volume of the two or more coils is minimized subject to a condition that includes a field homogeneity tolerance factor for a strength of an MR magnetic field during the MR imaging.

11. The RT system of claim 9, wherein the radii and spatial locations of the two or more coils of a given coil ensemble are based on at least one of patient clearance, a separation to allow for additional structures used for operating the MRI scanner, and a clearance to rotate the at least two magnet components.

12. A method for performing radiation treatment and at least one of patient setup verification, radiation treatment delivery, post treatment review and Magnetic Resonance (MR) imaging by using a Magnetic Resonance Imaging (MRI) scanner coupled to a radiation source that is coupled to a gantry that is rotatable and comprises a radiation source head, the radiation source being configured to generate a treatment beam for an object during use, the treatment beam having a treatment beam direction from the radiation source head to the object, and the MRI scanner being configured to perform the MR imaging and including at least two magnet components, the method comprising:

performing patient setup for a treatment location of the object with respect to the radiation source;

moving the at least two magnet components around the object via rotation of the gantry to image at least one region of the object within an imaging target volume before, during, or after treatment with the treatment beam, the at least two magnet components comprising two or more coils that together form a coil ensemble that creates the imaging target volume having an ellipsoidal shape with a first elliptical cross-section in a first plane and a second elliptical cross-section in a second plane orthogonal to the first plane, the first elliptical cross-section having a first major axis and a first minor axis and the second elliptical cross-section having a second major axis and a second minor axis, where the second minor axis is smaller than both the first major axis and the first minor axis;

positioning the at least two magnet components relative to the treatment beam such that the first elliptical cross-section of the imaging target volume is orthogonal to the treatment beam direction and in a beam's eye view of the treatment beam;

obtaining MR images and adjusting the patient setup based on the MR images;

applying radiation treatment to the object simultaneously with the MR imaging; and performing further MR imaging for the post treatment review of the object.

13. The method of claim 12, wherein at least one of the at least two magnet components is movably adjustable, and the method further comprises operating in a first operation mode in which the at least one the at least two magnet components is moved away from the object to perform imaging with the imaging target volume; and operating in a second operation mode in which the at least one of the at least two magnet components is moved closer to the object to perform imaging with a larger field of view than in the first operation mode.

14. The method of claim 12, wherein the method further comprises using a processor that is configured to perform single slice reconstruction on MRI imaging data obtained for the object assuming a non-uniform magnetic field is generated by the MRI scanner and based on prior knowledge of a spatial distribution of inhomogeneities of the magnetic field for a second region that includes and extends beyond the at least one region of the object.

15. The method of claim 12, wherein the at least two magnet components are mounted such that a magnetic field in the imaging volume is oriented in-line with the treatment beam thereby preserving the capability for kV imaging, and kV imaging components are mounted and oriented at 90° with respect to the treatment beam direction; and the method further comprises performing dual MRI and X-ray kV imaging.

16. The method of claim 15, wherein the method further comprises performing the dual MRI and X-ray kV imaging during rotation of the radiation source and the at least two magnet components around the object.

17. The method of claim 15, wherein an x-ray megavoltage (MV) panel detector is mounted to face the treatment beam during the dual MRI and X-ray MV imaging.

18. The method of claim 12, wherein the method comprises selecting radii and spatial locations for the two or more coils of the soil ensemble for optimizing at least one of coil power dissipation, total volume of the two or more coils, coil conductor mass, and a physical footprint of the coil ensemble.

19. The RT system of claim 18, wherein the total volume of the two or more coils is minimized subject to a condition that includes a field homogeneity tolerance factor for a strength of an MR magnetic field during the MR imaging.

20. The RT system of claim 18, wherein the radii and spatial locations of the two or more coils of a given coil ensemble are based on at least one of patient clearance, a separation to allow for additional structures used for operating the MRI scanner, and a clearance to rotate the at least two magnet components.

21. The method of claim 12, wherein the method further comprises configuring a processor to execute instructions to cause the MRI scanner to perform multi-slice MR imaging for the object by rotating the MRI scanner in unison with the gantry and obtaining multiple images at different gantry angles.

22. A computer readable medium comprising a plurality of instructions that are executable on a processor of a system for adapting the system to implement a method for performing radiation treatment and at least one of patient setup verification, radiation treatment delivery, post treatment review and Magnetic Resonance (MR) imaging by using a Magnetic Resonance Imaging (MRI) scanner coupled to a radiation source that is coupled to a gantry that is rotatable and comprises a radiation source head, the radiation source being configured to generate a treatment beam for an object during use, the treatment beam having a treatment beam direction from the radiation source head to the object, and the MRI scanner being configured to perform the MR imaging and including at least two magnet components, the method comprising:

performing patient setup for a treatment location of the object with respect to the radiation source;

moving the at least two magnet components around the object via rotation of the gantry to image at least one region of the object within an imaging target volume before, during or after treatment with the treatment beam, the at least two magnet components comprising two or more coils that together form a coil ensemble that creates the imaging target volume having an ellipsoidal shape with a first elliptical cross-section in a first plane and a second elliptical cross-section in a second plane orthogonal to the first plane, the first elliptical cross-section having a first major axis and a first minor axis and the second elliptical cross-section having a second major axis and a second minor axis, where the second minor axis is smaller than both the first major axis and the first minor axis;

positioning the at least two magnet components relative to the treatment beam such that the first elliptical cross-section of the imaging target volume is orthogonal to the treatment beam direction and in a beam's eye view of the treatment beam;

obtaining MR images and adjusting the patient setup based on the MR images;

applying radiation treatment to the object simultaneously with the MR imaging; and performing further MR imaging for the post treatment review of the object.

\* \* \* \* \*

UNITED STATES PATENT AND TRADEMARK OFFICE
CERTIFICATE OF CORRECTION

PATENT NO. : 10,596,393 B2
APPLICATION NO. : 14/417631
DATED : March 24, 2020
INVENTOR(S) : Stanescu et al.

Page 1 of 1

It is certified that error appears in the above-identified patent and that said Letters Patent is hereby corrected as shown below:

In the Claims

Claim 4, Column 35, Line 29, "...the duel MRI..." should read -- the dual MRI --.

Claim 19, Column 37, Line 18, "...The RT system..." should read -- The method --.

Claim 20, Column 37, Line 22, "...The RT system..." should read -- The method --.

Signed and Sealed this
Fourth Day of August, 2020

Andrei Iancu
*Director of the United States Patent and Trademark Office*